(12) United States Patent
Terry et al.

(10) Patent No.: US 8,746,240 B2
(45) Date of Patent: Jun. 10, 2014

(54) ACTIVATION TRIGGER FOR A PERSONAL VAPORIZING INHALER

(75) Inventors: Nathan Andrew Terry, San Francisco, CA (US); Noah Mark Minskoff, Salt Lake City, UT (US)

(73) Assignee: Nate Terry & Michael Edward Breede, Ridgefield, CT (US)

( * ) Notice: Subject to any disclaimer, the term of this patent is extended or adjusted under 35 U.S.C. 154(b) by 1008 days.

(21) Appl. No.: 12/780,872

(22) Filed: May 15, 2010

(65) Prior Publication Data

US 2011/0277756 A1    Nov. 17, 2011

(51) Int. Cl.
*A61M 15/06* (2006.01)
*A24F 47/00* (2006.01)
*A61M 11/04* (2006.01)

(52) U.S. Cl.
CPC ............. *A61M 15/06* (2013.01); *A24F 47/002* (2013.01); *A61M 11/04* (2013.01)
USPC ............ 128/202.21; 128/200.11; 128/200.12; 128/203.12; 128/203.16; 128/204.13; 131/273

(58) Field of Classification Search
CPC ... A27F 47/002; A27F 47/004; A27F 47/006; A27F 47/008; A61M 15/00; A61M 11/00
USPC ............. 128/200.11–200.13, 200.14–200.23, 128/200.24, 202.21, 203.12–204.14, 204.17
See application file for complete search history.

(56) References Cited

U.S. PATENT DOCUMENTS

| | | | |
|---|---|---|---|
| 4,177,799 A | * | 12/1979 | Masreliez ..................... 600/554 |
| 4,429,703 A | | 2/1984 | Haber |
| 4,735,217 A | | 4/1988 | Gerth et al. |
| 4,771,796 A | | 9/1988 | Myer |
| 4,922,901 A | | 5/1990 | Brooks et al. |
| 4,947,874 A | | 8/1990 | Brooks et al. |
| 4,947,875 A | | 8/1990 | Brooks et al. |
| 4,991,596 A | | 2/1991 | Lawrence et al. |
| 5,060,671 A | | 10/1991 | Counts et al. |
| 5,261,424 A | | 11/1993 | Sprinkel, Jr. |
| 5,269,327 A | | 12/1993 | Counts et al. |
| 5,353,813 A | | 10/1994 | Deevi et al. |
| 5,408,574 A | | 4/1995 | Deevi et al. |
| 5,573,692 A | | 11/1996 | Das et al. |

(Continued)

OTHER PUBLICATIONS

International Search Report and Written Opinion of PCT/US2011/036252 issued Jan. 2, 2012, 9 pages.

(Continued)

*Primary Examiner* — Justine Yu
*Assistant Examiner* — Valerie L Skorupa
(74) *Attorney, Agent, or Firm* — The Neudeck Law Firm, LLC

(57) ABSTRACT

A personal vapor inhaling unit is disclosed. An electronic flameless vapor inhaler unit that may simulate a cigarette has a cavity that receives a cartridge in the distal end of the inhaler unit. The cartridge brings a substance to be vaporized in contact with a wick. When the unit is activated, and the user provides suction, the substance to be vaporized is drawn out of the cartridge, through the wick, and is atomized by the wick into a cavity containing a heating element. The heating element vaporizes the atomized substance. The vapors then continue to be pulled by the user through a mouthpiece and mouthpiece cover where they may be inhaled.

20 Claims, 25 Drawing Sheets

(56) References Cited

U.S. PATENT DOCUMENTS

| | | |
|---|---|---|
| 5,666,977 A | 9/1997 | Higgins et al. |
| 5,730,158 A | 3/1998 | Collins et al. |
| 5,893,371 A | 4/1999 | Rose et al. |
| 6,024,097 A | 2/2000 | Von Wielligh |
| 6,095,153 A | 8/2000 | Kessler et al. |
| 6,125,853 A | 10/2000 | Susa et al. |
| 6,155,268 A | 12/2000 | Takeuchi |
| 6,196,218 B1 | 3/2001 | Voges |
| 6,854,470 B1 | 2/2005 | Pu |
| 6,902,397 B2 * | 6/2005 | Farrell et al. .................. 433/29 |
| 7,665,460 B2 * | 2/2010 | Lindsay et al. .......... 128/200.14 |
| 7,779,835 B2 * | 8/2010 | Hamano .................. 128/203.12 |
| 7,975,341 B2 * | 7/2011 | Cai et al. ........................ 15/22.1 |
| 2002/0136886 A1 | 9/2002 | He et al. |
| 2004/0055613 A1 | 3/2004 | Horian |
| 2006/0196518 A1 | 9/2006 | Hon |
| 2006/0283468 A1 | 12/2006 | Lipowiez |
| 2007/0240711 A1 * | 10/2007 | Hamano .................. 128/203.12 |
| 2007/0267031 A1 | 11/2007 | Hon |
| 2008/0131834 A1 * | 6/2008 | Shepherd et al. ............... 433/29 |
| 2008/0276947 A1 | 11/2008 | Martzel |
| 2008/0302375 A1 | 12/2008 | Andersson et al. |
| 2009/0095311 A1 | 4/2009 | Han |
| 2009/0095312 A1 | 4/2009 | Herbrich et al. |
| 2009/0126745 A1 | 5/2009 | Hon |
| 2009/0165808 A1 | 7/2009 | Melahropoulos |
| 2009/0253105 A1 * | 10/2009 | Lepine ......................... 434/127 |
| 2009/0260641 A1 | 10/2009 | Monsees et al. |
| 2009/0283103 A1 | 11/2009 | Nielsen et al. |
| 2010/0006113 A1 | 1/2010 | Urtsev et al. |

OTHER PUBLICATIONS

International Search Report and Written Opinion of PCT/US2011/036259 issued Jan. 2, 2012, 9 pages.
International Search Report and Written Opinion of PCT/US2011/036267 issued Jan. 10, 2012, 9 pages.
International Search Report and Written Opinion of PCT/US2011/036275 issued Jan. 10, 2012, 9 pages.
International Search Report and Written Opinion of PCT/US2011/036283 issued Jan. 4, 2012, 9 pages.
International Search Report and Written Opinion of PCT/US2011/036396 issued Jan. 17, 2012, 9 pages.
International Search Report and Written Opinion of PCT/US2011/036399 issued Jan. 18, 2012, 10 pages.
International Search Report and Written Opinion of PCT/US2011/032016 issued Dec. 20, 2011, 10 pages.
International Search Report and Written Opinion of PCT/US2011/032025 issued Dec. 20, 2011, 10 pages.
International Search Report and Written Opinion of PCT/US2011/036600 issued Jan. 18, 2012, 12 pages.
International Search Report and Written Opinion of PCT/US2011/036605 issued Jan. 18, 2012, 10 pages.
International Search Report and Written Opinion of PCT/US2011/036609 issued Jan. 19, 2012, 11 pages.
International Search Report and Written Opinion of PCT/US2011/036614 issued Jan. 19, 2012, 11 pages.

* cited by examiner

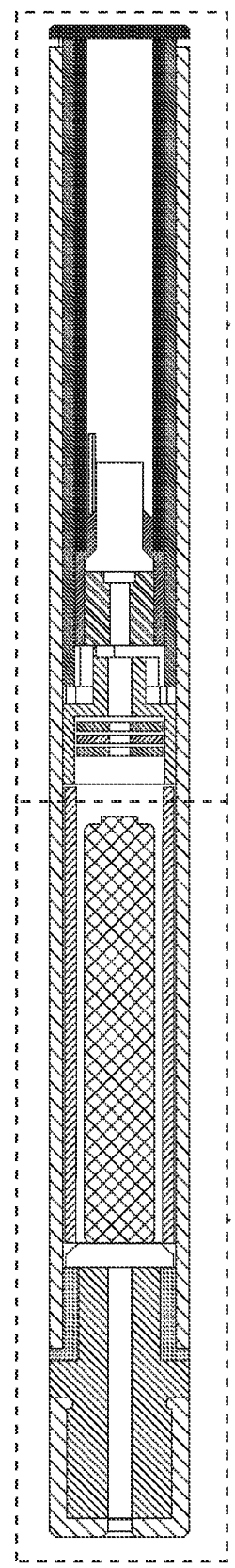

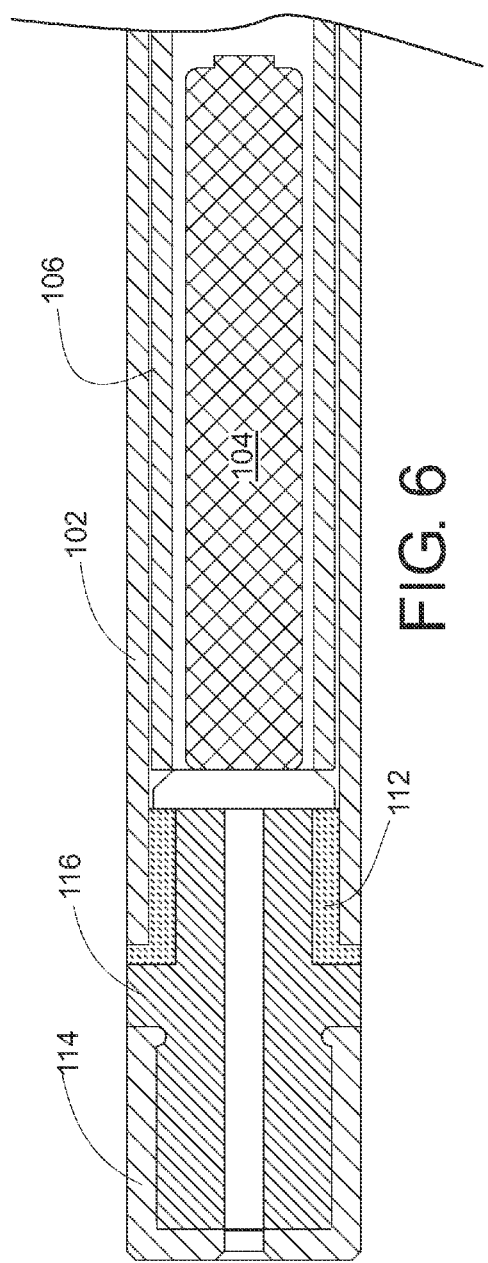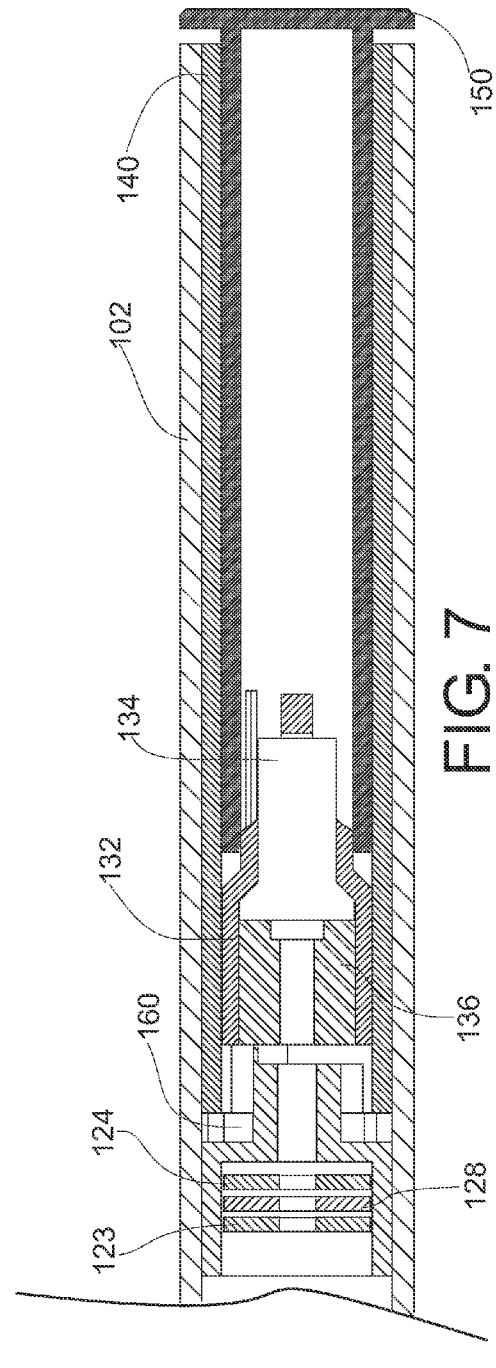

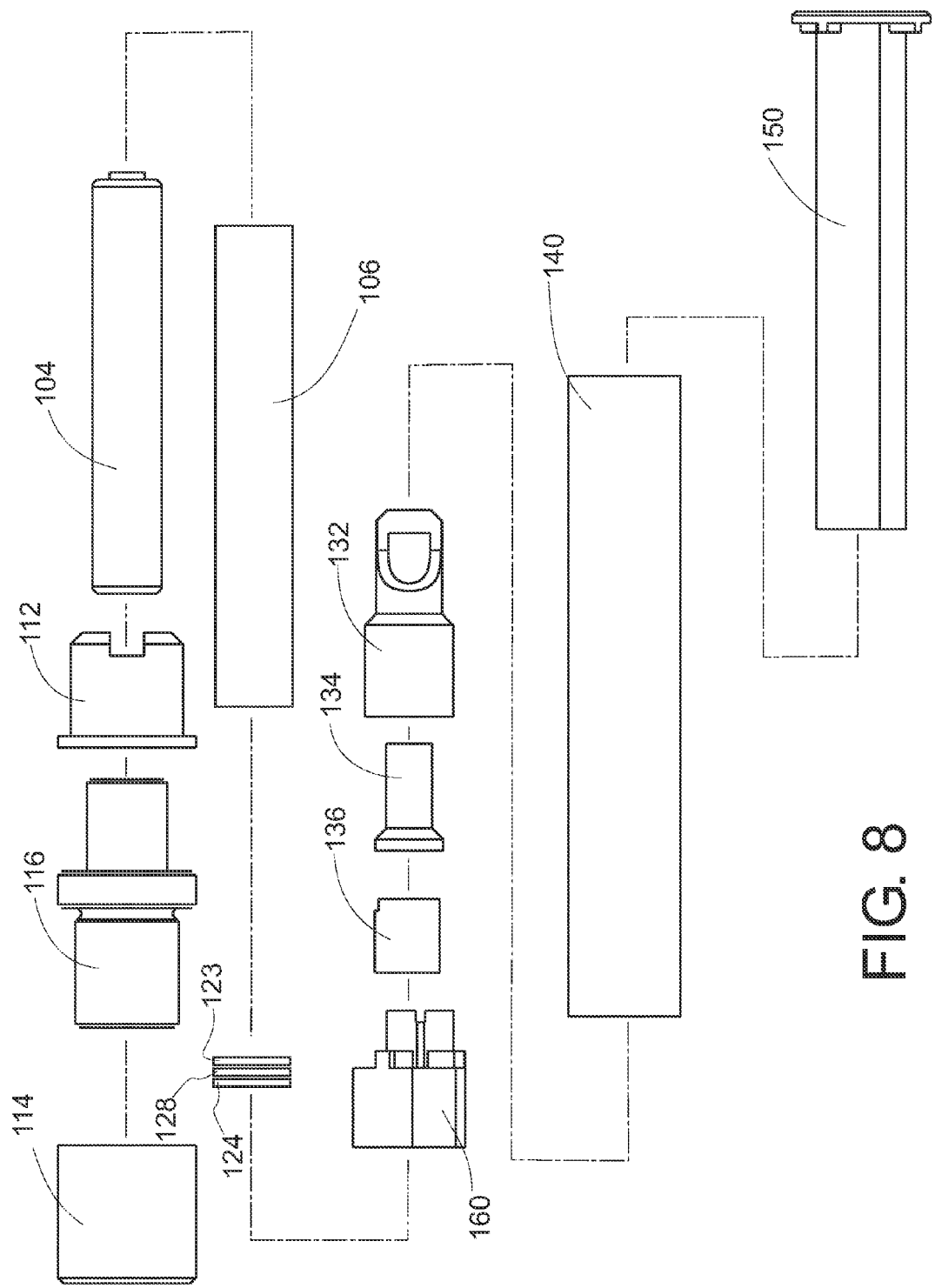

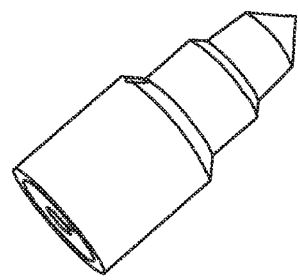
FIG. 54
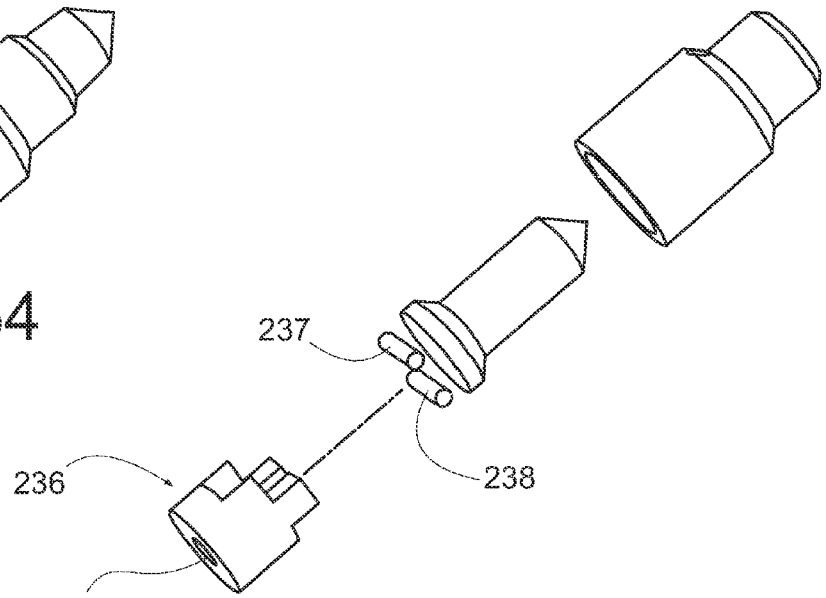
FIG. 55
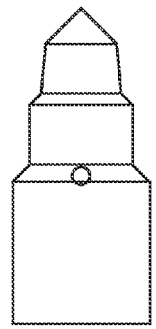
FIG. 56
FIG. 57
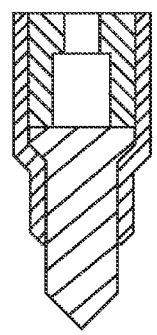
FIG. 58

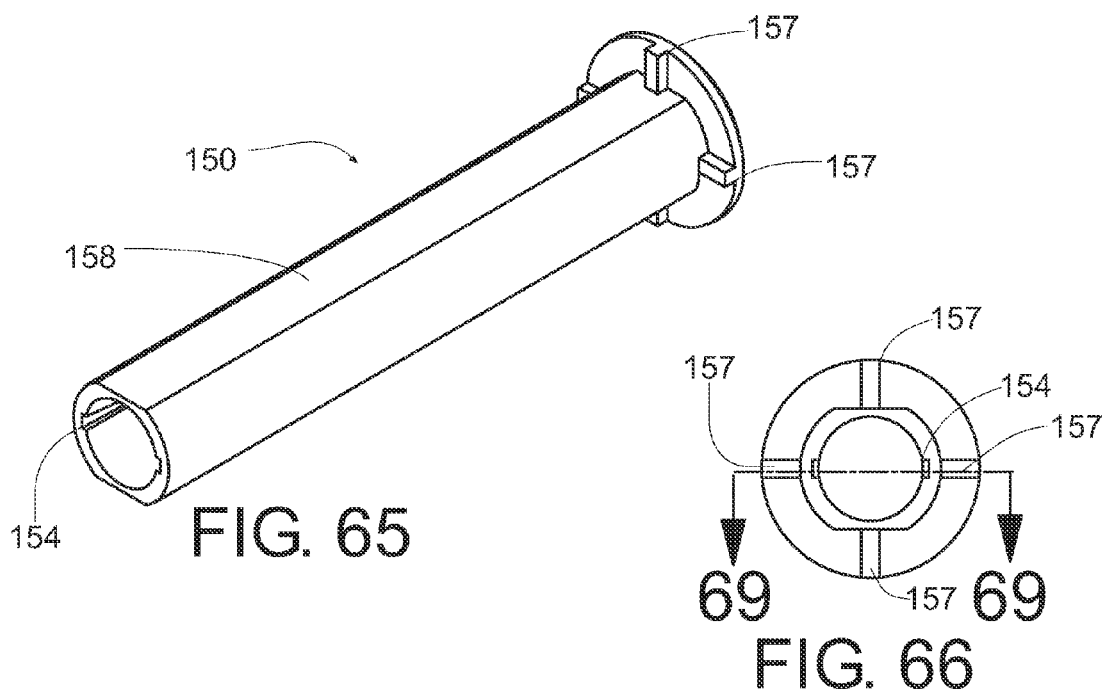
FIG. 65
FIG. 66
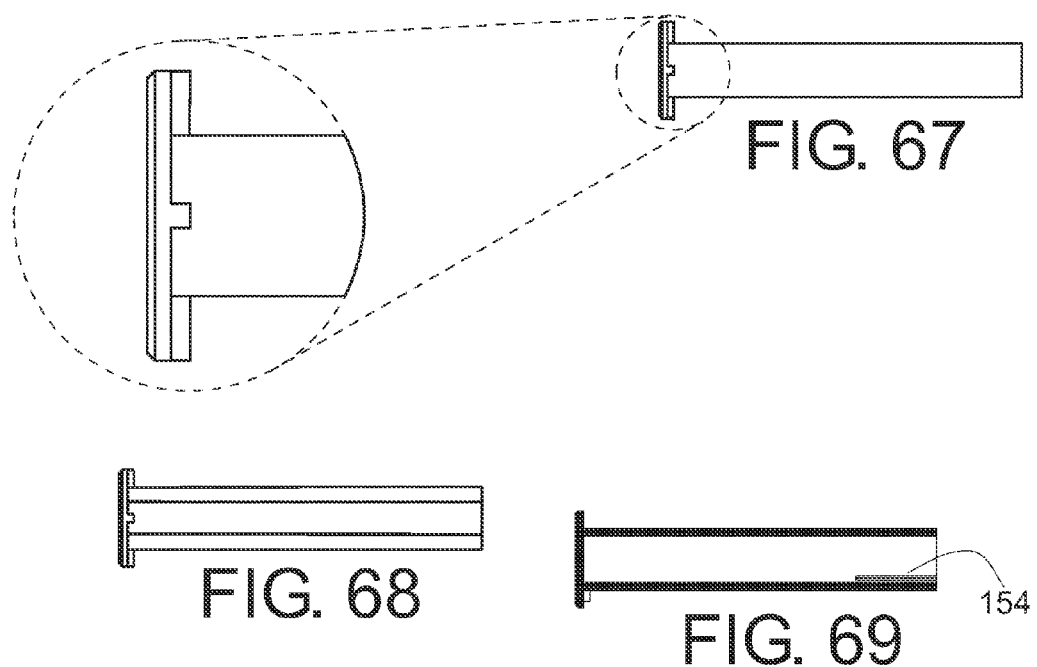
FIG. 67
FIG. 68
FIG. 69

ACTIVATION TRIGGER FOR A PERSONAL VAPORIZING INHALER

CROSS-REFERENCE TO RELATED APPLICATIONS

This application is related to the following U.S. applications filed on or about the same day as the present application: Ser. No. 12/780,871, entitled "PERSONAL VAPORIZING INHALER WITH MOUTHPIECE COVER"; Ser. No. 12/780,873, entitled "PERSONAL VAPORIZING INHALER CARTRIDGE"; Ser. No. 12/780,874, entitled "ATOMIZER-VAPORIZER FOR A PERSONAL VAPORIZING INHALER"; Ser. No. 12/780,875, entitled "PERSONAL VAPORIZING INHALER WITH INTERNAL LIGHT SOURCE"; Ser. No. 12/780,876, entitled "DATA LOGGING PERSONAL VAPORIZING INHALER"; and, Ser. No. 12/780,877, entitled "PERSONAL VAPORIZING INHALER ACTIVE CASE"; whose applications are hereby incorporated herein by reference for all purposes.

TECHNICAL FIELD

This invention relates to personal vapor inhaling units and more particularly to an electronic flameless vapor inhaler unit that may simulate a cigarette or deliver nicotine and other medications to the oral mucosa, pharyngeal mucosa, tracheal, and pulmonary membranes.

BACKGROUND

An alternative to smoked tobacco products, such as cigarettes, cigars, or pipes is a personal vaporizer. Inhaled doses of heated and atomized flavor provide a physical sensation similar to smoking. However, because a personal vaporizer is typically electrically powered, no tobacco, smoke, or combustion is usually involved in its operation. For portability, and to simulate the physical characteristics of a cigarette, cigar, or pipe, a personal vaporizer may be battery powered. In addition, a personal vaporizer may be loaded with a nicotine bearing substance and/or a medication bearing substance. The personal vaporizer may provide an inhaled dose of nicotine and/or medication by way of the heated and atomized substance. Thus, personal vaporizers may also be known as electronic cigarettes, or e-cigarettes. Personal vaporizers may be used to administer flavors, medicines, drugs, or substances that are vaporized and then inhaled.

BRIEF DESCRIPTION OF THE DRAWINGS

FIG. 5 is a figure map of FIGS. 6 and 7.

FIG. 6 is a cross-section of the proximal portion of a personal vaporizer unit along the cut line shown in FIG. 2.

FIG. 7 is a cross-section of the distal portion of a personal vaporizer unit along the cut line shown in FIG. 2.

FIG. 8 is an exploded side view of components of a personal vaporizer unit.

FIG. 54 is a perspective view of an atomizer housing and wicks of a personal vaporizer unit.

FIG. 55 is an exploded view of the atomizer housing, wire guides, and wicks of FIG. 54.

FIG. 56 is a side view of the atomizer housing and wicks of FIG. 54.

FIG. 57 is a distal end view of the atomizer housing and wicks of FIG. 54.

FIG. 58 is a cross-section of the atomizer housing and wicks along the cut line shown in FIG. 57.

FIG. 65 is a perspective view of a cartridge of a personal vaporizer unit.

FIG. 66 is a proximal end view of the cartridge of FIG. 65.

FIG. 67 is a side view of the cartridge of FIG. 65.

FIG. 68 is a top view of the cartridge of FIG. 65.

FIG. 69 is a cross-section of the cartridge along the cut line shown in FIG. 66.

DETAILED DESCRIPTION

Figure 1:
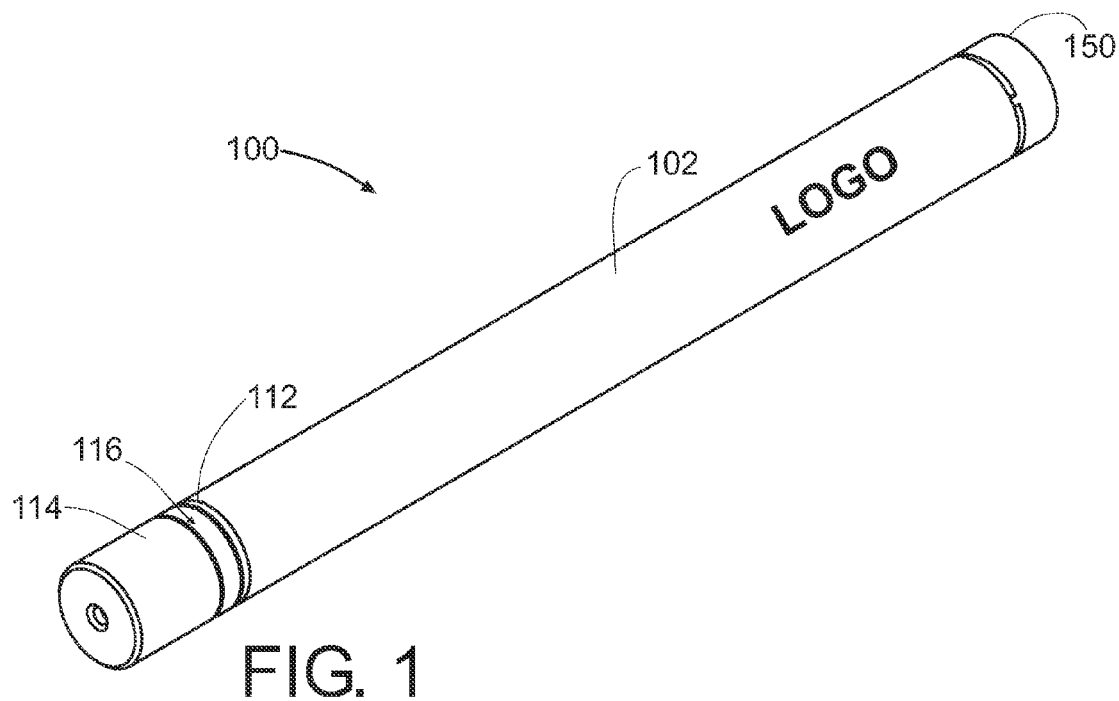
FIG. 1 is a perspective view of a personal vaporizer unit.

In an embodiment a personal vaporizer unit comprises a mouthpiece configured for contact with the mouth of a person. At least part of this mouthpiece has an antimicrobial surface. This mouthpiece may also comprise silicone rubber, thermoplastic elastomer, organosilane, silver impregnated polymer, silver impregnated thermoplastic elastomer, and/or polymer. The mouthpiece may be removed from the personal vaporizing for washing or replacement, without using a tool. The mouthpiece may be provided in different colors. Designs or other patterns may be visible on the outside of the mouthpiece.

In an embodiment, a personal vaporizer unit comprises a first conductive surface configured to contact a first body part of a person holding the personal vaporizer unit, and a second conductive surface, conductively isolated from the first conductive surface, configured to contact a second body part of the person. When the personal vaporizer unit detects a change in conductivity between the first conductive surface and the second conductive surface, a vaporizer is activated to vaporize a substance so that the vapors may be inhaled by the person holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory.

In an embodiment, a personal vaporizer unit comprises a chamber configured to receive a cartridge. The cartridge may hold a substance to be vaporized. The chamber may be configured at the distal end of the personal vaporizer unit. A user may inhale the vaporized substance at the proximal end of the personal vaporizer unit. At least one space between the exterior surface of the cartridge, and an interior surface of the chamber, may define a passage for air to be drawn from outside the personal vaporizer unit, near the distal end, through the personal vaporizer unit to be inhaled by the user along with the vaporized substance. The personal vaporizer unit may also include a puncturing element that breaks a seal on the cartridge to allow a substance in the cartridge to be vaporized. An end surface of the cartridge may be translucent to diffuse light produced internally to the personal vaporizer unit. The translucent end may be etched or embossed with letters, symbols, or other indicia that are illuminated by the light produced internally to the personal vaporizer unit.

In an embodiment, a personal vaporizer unit comprises a first wick element and a second wick element having a porous ceramic. The first wick element is adapted to directly contact a liquid held in a reservoir. The reservoir may be contained by a cartridge that is removable from the personal vaporizer unit. A heating element is disposed through the second wick element. An air gap is defined between the first wick element and the second wick element with the heating element exposed to the air gap. Air enters the first wick element through a hole in a housing holding the first wick element.

In an embodiment, a personal vaporizer unit comprises a light source internal to an opaque cylindrical housing that approximates the appearance of a smoking article. A cylindrical light tube is disposed inside the opaque cylindrical housing to conduct light emitted by the light source to an end of the opaque cylindrical housing. This allows the light to be visible outside of the opaque cylindrical housing of the vaporizer.

In an embodiment, a personal vaporizer unit comprises a microprocessor, memory, and a connector. The connector outputs data stored in the memory. The microprocessor may gather, and store in the memory, information including, but not limited to, the number of cycles the device has been triggered, the duration of the cycles, the number cartridges of fluid that are delivered. The microprocessor may also gather and store times and dates associated with the other information gathered and stored. The microprocessor may detect an empty cartridge by detecting a specific change in resistance between a wick and a housing that is equivalent to a "dry wick", and thus signifies an empty cartridge.

In an embodiment, a case comprises a cradle adapted to hold a personal vaporizer unit. The personal vaporizer unit has dimensions approximating a smoking article. The case includes a battery and at least two contacts. The two contacts may form an electrical contact with the personal vaporizer unit when the personal vaporizer unit is in the cradle. The two contacts may conduct charge from the battery to the personal vaporizer unit to charge the personal vaporizer unit. The case may also download and store data retrieved from the personnel vaporizing unit. The case may download and store this data via the at least two contacts. The case may send this data to a computer via wired or wireless links. The case may have more than one cradle and sets of contacts (e.g., two sets of two contacts in order to hold and charge two personal vaporizer units).

FIG. 1 is a perspective view of a personal vaporizer unit. In FIG. 1, personal vaporizer unit 100 comprises outer main shell 102, mouthpiece cover 114, mouthpiece 116, and mouthpiece insulator 112. The mouthpiece 116 and mouthpiece cover 114 define the proximal end of personal vaporizer unit 100. The opposite end of personal vaporizer unit 100 will be referred to as the distal end. A cartridge 150 may be inserted into the distal end of personal vaporizer unit 100. Cartridge 150 may hold the substance to be vaporized by personal vaporizer unit 100. The substance after vaporizing may be inhaled by a user holding the personal vaporizer unit 100. The substance may be in the form of a liquid or gel.

Figure 2:
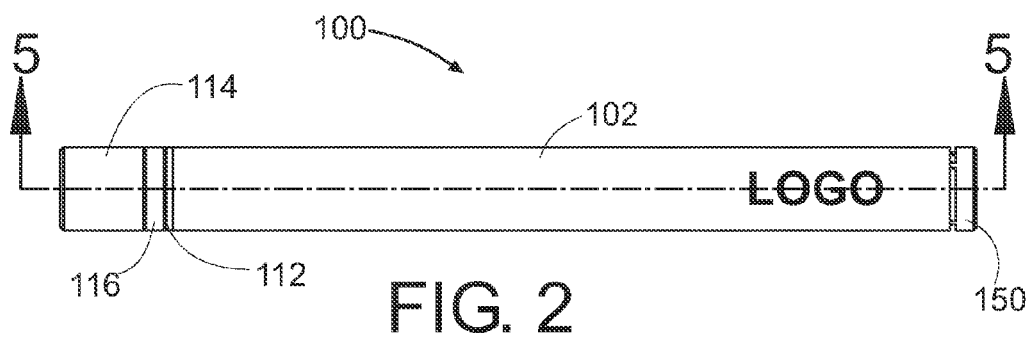
FIG. 2 is a side view of a personal vaporizer unit.

FIG. 2 is a side view of a personal vaporizer unit. FIG. 2 illustrates personal vaporizer unit 100 as viewed from the side. FIG. 2 illustrates personal vaporizer unit 100 comprising outer main shell 102, mouthpiece cover 114, mouthpiece 116, and mouthpiece insulator 112. FIG. 2 also illustrates cartridge 150 inserted into the distal end of personal vaporizer unit 100.

Figure 3:
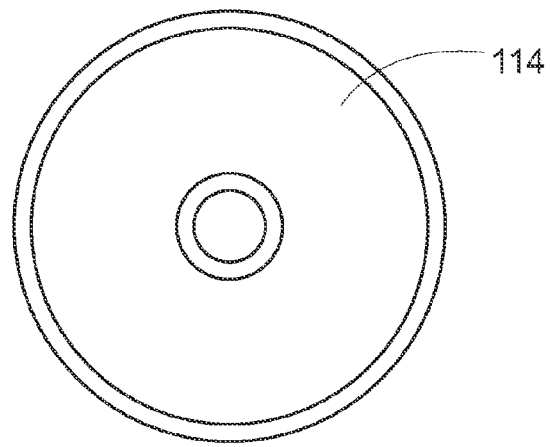
FIG. 3 is an end view of the proximal end of a personal vaporizer unit.
Figure 4A:
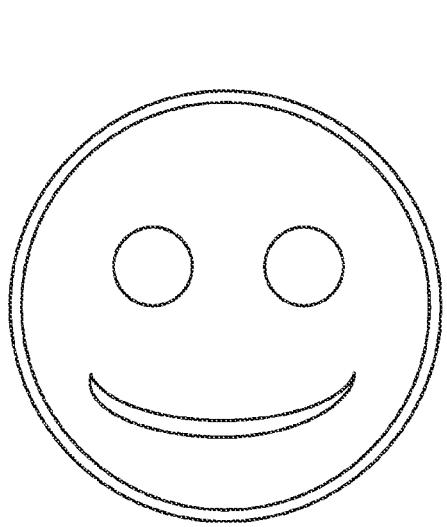
FIG. 4A is an end view of the distal end of a personal vaporizer unit having an embossed cartridge.
Figure 4:
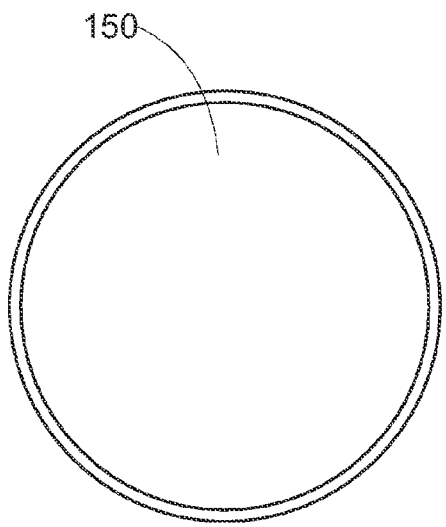
FIG. 4 is an end view of the distal end of a personal vaporizer unit.

FIG. 3 is an end view of the proximal end of a personal vaporizer unit. FIG. 3 shows the proximal end view of personal vaporizer unit 100 comprising mouthpiece cover 114. FIG. 4 is an end view of the distal end of a personal vaporizer unit. FIG. 4 shows the distal end view personal vaporizer unit 100 comprising the visible portion of cartridge 150. FIG. 4A is an alternative end view of personal vaporizer unit 100 comprising a visible portion of cartridge 150 that has visible logos, letters, or other symbols. These visible logos, letters, or other symbols may be illuminated or backlit by a light source internal to the personal vaporizer unit 100. The light source may be activated intermittently under the control of a microprocessor or other electronics internal to personal vaporizer unit 100. The light source may be activated in such a manner as to simulate the glowing ash of a cigar or cigarette.

FIG. 5 is a figure map of FIGS. 6 and 7. FIG. 6 is a cross-section of the proximal portion of a personal vaporizer unit along the cut line shown in FIG. 2. In FIG. 6, the proximal portion of personal vaporizer unit 100 comprises mouthpiece cover 114, mouthpiece 116, mouthpiece insulator 112, outer main shell 102, battery support 106, and battery 104. The mouthpiece cover 114 surrounds and is engaged with the distal end of mouthpiece 116. Mouthpiece 116 and outer main shell 102 are preferably made of an electrically conductive material(s). Mouthpiece 116 is separated from outer main shell 102 by mouthpiece insulator 112. Mouthpiece 116 and outer main shell 102 are thus electrically isolated from each other by mouthpiece insulator 112.

In an embodiment, personal vaporizer unit 100 is configured such that other main shell 102 comprises a first conductive surface configured to contact a first body part of a person holding personal vaporizer unit 100. Mouthpiece 116 comprises a second conductive surface, which is conductively isolated from the first conductive surface. This second conductive surface is configured to contact a second body part of the person. When personal vaporizer unit 100 detects a change in conductivity between the first conductive surface and the second conductive surface, a vaporizer internal to personal vaporizer unit 100 is activated to vaporize a substance in cartridge 150 so that the vapors may be inhaled by the person holding personal vaporizer unit 100. The first body part and the second body part may be a lip or parts of a hand(s). The two conductive surfaces of outer main shell 102 and mouthpiece 116, respectively, may also be used to charge battery 104 contained in the personal vaporizer unit 100. The two conductive surfaces of outer main shell 102 and mouthpiece 116, respectively, may also be used to output (or input) data stored (or to be stored) in a memory (not shown).

Battery support 106 functions to hold battery 104 in a position which is fixed relative to our main shell 102. Battery support 106 is also configured to allow air and vaporized substance to pass from the distal end of personal vaporizer unit 100 past battery 104 along one or more passageways. After air and the vapors of the vaporized substance pass by battery 104, they may pass through openings in mouthpiece 116, mouthpiece cover 114, and mouthpiece insulator 112, to be inhaled by a user.

FIG. 7 is a cross-section of the distal portion of a personal vaporizer unit along the cut line shown in FIG. 2. In FIG. 7, the distal end portion of personal vaporizer unit 100 comprises outer main shell 102, light pipe sleeve 140, and atomizer housing 132, distal wick 134, proximal wick 136, PC board 123, PC board 124, spacer 128, and main housing 160. FIG. 7 also illustrates cartridge 150 inserted into the distal end of personal vaporizer unit 100. As can be seen in FIG. 7, cartridge 150 may hold a substance (e.g., a liquid or gel) in direct contact with distal wick 134. The substance may be drawn through distal wick 134 to be vaporized inside atomizer assembly. The atomizer assembly comprises atomizer housing 132, distal wick 134, proximal wick 136, and a heating element (not shown).

Figure 9:
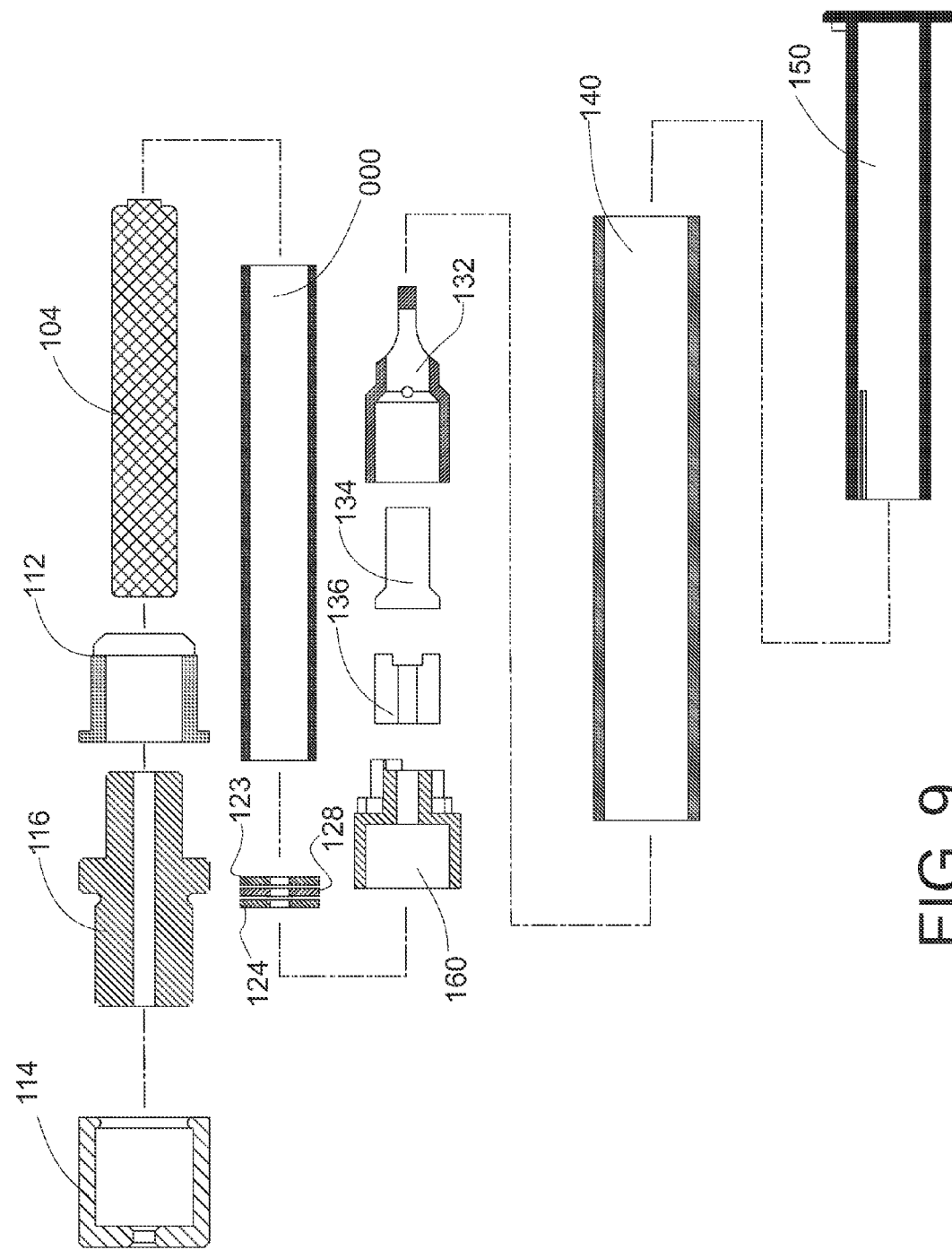
FIG. 9 is an exploded cross-section of components of a personal vaporizer unit along the cut line shown in FIG. 2.

FIG. 8 is an exploded side view of components of a personal vaporizer unit. FIG. 9 is an exploded cross-section of components of a personal vaporizer unit along the cut line shown in FIG. 2.

In FIGS. 8 and 9, personal vaporizer unit 100 comprises (from left to right) mouthpiece cover 114, mouthpiece 116, mouthpiece insulator 112, battery 104, battery support 106, PC board 123, spacer 128, PC board 124, main housing 160, proximal wick 136, distal wick 134, atomizer housing 132, light pipe sleeve 140, and cartridge 150. Mouthpiece cover 114 surrounds and covers the proximal end of mouthpiece 116. The distal end of mouthpiece 116 is inserted into mouthpiece insulator 112. Battery 104 is held in place by battery support 106. PC board 123, spacer 128 and PC board 124 are disposed within main housing 160. Proximal wick 136 and distal wick 134 are disposed within atomizer housing 132.

Atomizer housing 132 (and therefore proximal wick 136, distal wick 134) are disposed inside light pipe sleeve 140 and main shell 102. (Note: for clarity, main shell 102 is not shown in FIGS. 8 and 9.) Light pipe sleeve 140 is disposed within main shell 102. Light pipe sleeve 140 is positioned such that light emitted from a light source mounted on PC board 124 may be conducted via light pipe sleeve 140 to a location where it is visible on the outside of personal vaporizer unit 100.

Cartridge 150 is disposed within light pipe sleeve 140. When assembled, a substance contained within cartridge 150 is held in direct contact with distal wick 134. When cartridge 150 is inserted into personal vaporizer unit 100 atomizer housing 132 or distal wick 134 may puncture a seal or cap that contains the substance to be vaporized within cartridge 150. Once punctured, the substance held within a reservoir of cartridge 150 may come in direct contact with distal wick 134.

Figure 10:
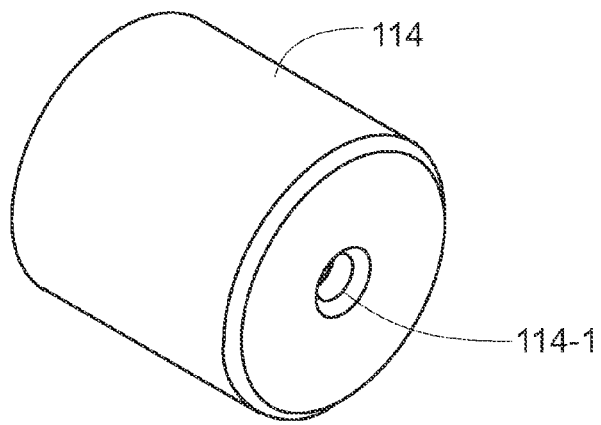
FIG. 10 is a perspective view of a mouthpiece cover of a personal vaporizer unit.
Figure 11:
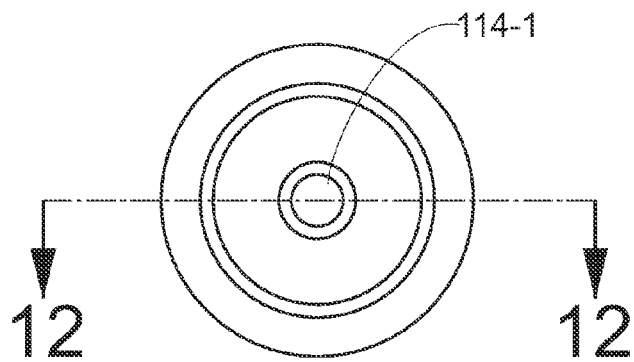
FIG. 11 is a distal end view of the mouthpiece cover of FIG. 10.
Figure 12:
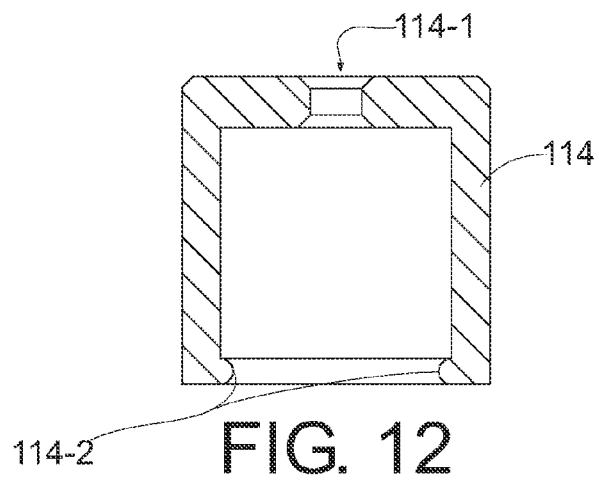
FIG. 12 is a cross-section of the mouthpiece cover along the cut line shown in FIG. 11.

FIG. 10 is a perspective view of a mouthpiece cover of a personal vaporizer unit. FIG. 11 is a distal end view of the mouthpiece cover of FIG. 10. FIG. 12 is a cross-section of the mouthpiece cover along the cut line shown in FIG. 11. As can be seen in FIGS. 10-12, mouthpiece cover 114 has an opening 114-1 that allows air and the vaporized substance to be drawn through mouthpiece cover 114. Mouthpiece cover 114 is configured for contact with the mouth of a person. In an embodiment, at least part of the mouthpiece cover has an antimicrobial surface. This antimicrobial surface of mouthpiece cover 114 may comprise, but is not limited to: silicone rubber, thermoplastic elastomer, organosilane, silver impregnated polymer, silver impregnated thermoplastic elastomer, and/or polymer. Mouthpiece cover 114 is also configured to be removable from personal vaporizer unit 100 by a user without the use of tools. This allows mouthpiece cover 114 to be replaced and/or washed. In an embodiment, mouthpiece cover 114 may be held in place on personal vaporizer unit 100 by annular ridge 114-2 which interfaces with a groove on mouthpiece 116 of personal vaporizer unit 100 to secure mouthpiece cover 114 in place. In another embodiment, mouthpiece cover 114 may be held in place on personal vaporizer unit 100 by a friction fit.

Figure 13:
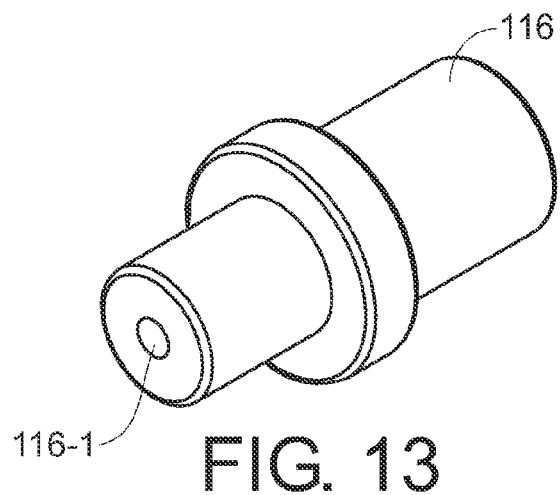
FIG. 13 is a perspective view of a mouthpiece of a personal vaporizer unit.
Figure 14:
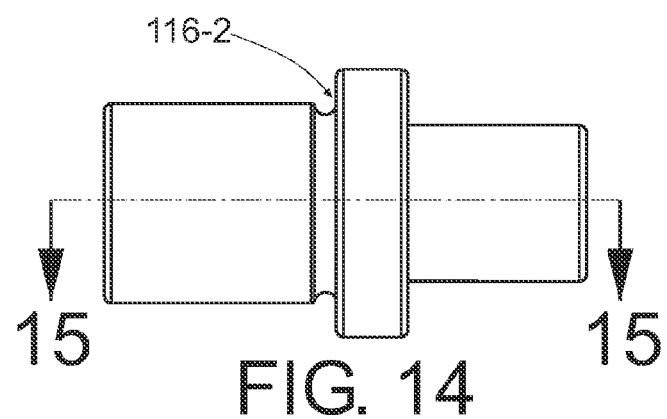
FIG. 14 is a side view of the mouthpiece of FIG. 13.
Figure 15:
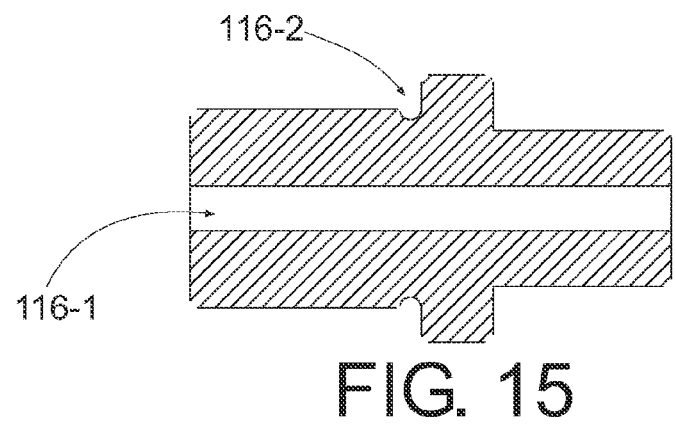
FIG. 15 is a cross-section of the mouthpiece along the cut line shown in FIG. 14.

FIG. 13 is a perspective view of a mouthpiece of a personal vaporizer unit. FIG. 14 is a side view of the mouthpiece of FIG. 13. FIG. 15 is a cross-section of the mouthpiece along the cut line shown in FIG. 14. As can be seen in FIGS. 13-15, mouthpiece 116 has a passageway 116-1 that allows air and the vaporized substance to be drawn through mouthpiece 116. Mouthpiece 116 may comprise a conductive surface or material configured to contact a first body part of a person holding personal vaporizer unit 100. This first body part may be part of a hand, or at least one lip of the person holding personal vaporizer unit 100. In an embodiment, mouthpiece 116 has an annular groove 116-2 around an outside surface. This groove is configured to receive annular ridge 114-2. Thus, annular groove 116-2 helps secure mouthpiece cover 114 to personal vaporizer unit 100.

Figure 16:
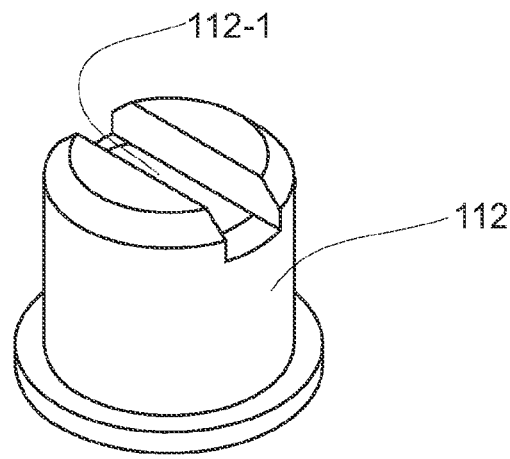
FIG. 16 is a perspective view of a mouthpiece insulator of a personal vaporizer unit.
Figure 17:
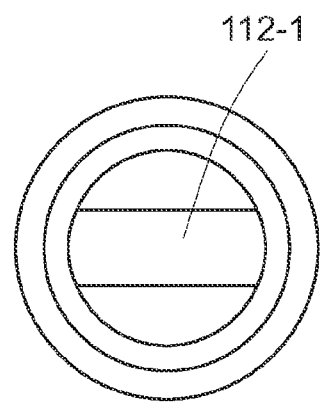
FIG. 17 is a distal end view of the mouthpiece insulator of FIG. 16.
Figure 18:
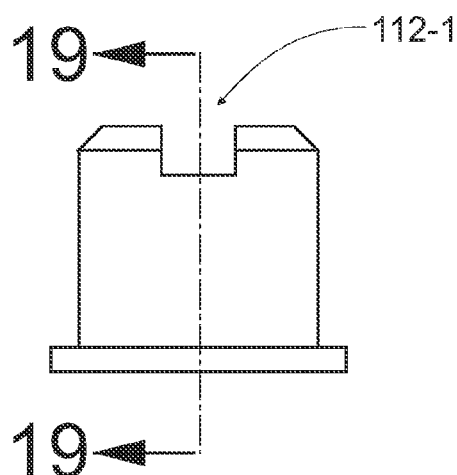
FIG. 18 is a side view of the mouthpiece insulator of FIG. 16.
Figure 19:
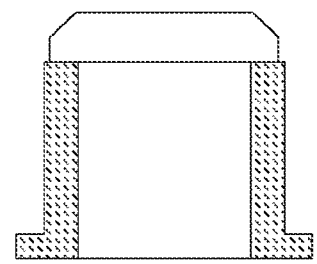
FIG. 19 is a cross-section of the mouthpiece insulator along the cut line shown in FIG. 18.

FIG. 16 is a perspective view of a mouthpiece insulator of a personal vaporizer unit. FIG. 17 is a distal end view of the mouthpiece insulator of FIG. 16. FIG. 18 is a side view of the mouthpiece insulator of FIG. 16. FIG. 19 is a cross-section of the mouthpiece insulator along the cut line shown in FIG. 18. As discussed previously, mouthpiece insulator 112 is disposed between main shell 102 and mouthpiece 116. As can be seen in FIGS. 16-18, mouthpiece insulator 112 has a passageway 112-1 that allows air and the vaporized substance to be drawn through mouthpiece insulator 112. Because mouthpiece insulator 112 is disposed between main shell 102 and mouthpiece 116, mouthpiece insulator 112 can electrically isolate main shell 102 and mouthpiece 116. Thus, in an embodiment, mouthpiece insulator 112 comprises, or is made of, a non-electrically conductive material. This electrical isolation between main shell 102 and mouthpiece 116 allow electrical impedance changes between main shell 102 and mouthpiece 116 to be detected.

For example, a first conductive surface on mouthpiece 116 may be configured to contact a first body part of a person holding personal vaporizer unit 100. A second conductive surface on main shell 102 (which is conductively isolated from said first conductive surface by mouthpiece insulator 112) may be configured to contact a second body part of the person. Personal vaporizer unit 100 may then activate in response to detecting a change in conductivity between the first conductive surface and the second conductive surface. In an embodiment, this change in conductivity may comprise a drop in impedance between the first conductive surface and the second conductive surface. In an embodiment, the change in conductivity may comprise a change in capacitance between the first conductive surface and the second conductive surface. The first body part may be a finger. The second body part may be a lip. The second body part may be a second finger. In an embodiment, the first conductive surface and the second conductive surfaces may be used to pass a charging current to battery 104. The first and second conductive surfaces may also be used to transfer data to or from personal vaporizer unit 100.

Figure 20:
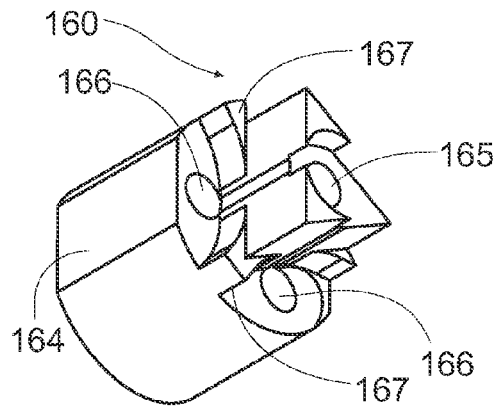
FIG. 20 is a perspective view of a main housing of a personal vaporizer unit.
Figure 21:
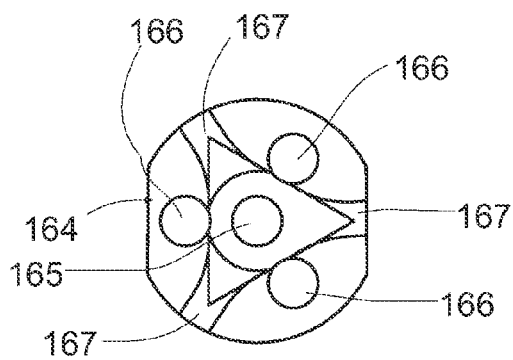
FIG. 21 is a distal end view of the main housing of FIG. 20.
Figure 22:
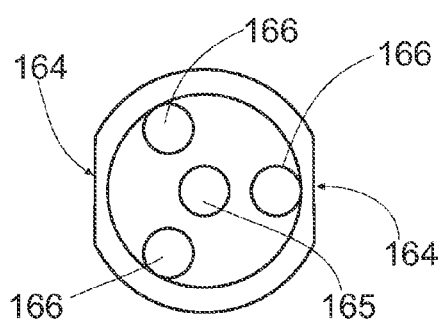
FIG. 22 is a proximal end view of the main housing of FIG. 20.
Figure 23:
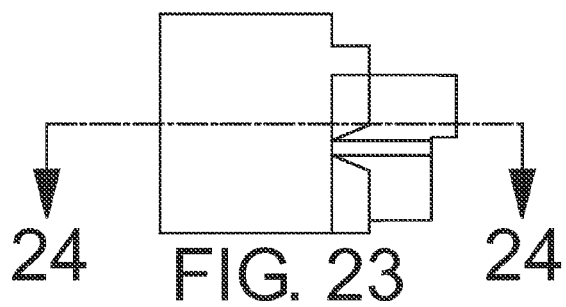
FIG. 23 is a side view of the main housing of FIG. 20.
Figure 24:
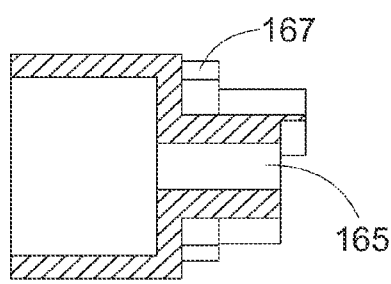
FIG. 24 is a cross-section of the main housing along the cut line shown in FIG. 23.

FIG. 20 is a perspective view of a main housing of a personal vaporizer unit. FIG. 21 is a distal end view of the main housing of FIG. 20. FIG. 22 is a proximal end view of the main housing of FIG. 20. FIG. 23 is a side view of the main housing of FIG. 20. FIG. 24 is a cross-section of the main housing along the cut line shown in FIG. 23. Main housing 160 is configured to hold PC-boards 123 and 124, and spacer 128. Main housing 160 is configured to fit within main shell 102 via a friction fit. Main housing 160 has several holes 166 that allow light generated by a light source(s) on PC-board 124 to pass. Once this light passes through holes 166, it may be coupled into light pipe sleeve 140 where it is conducted to a visible location on the outside of personal vaporizer unit 100.

Main housing 160 also has a hole 165 that allows an electrical conductor (not shown) to run from PC-board 123 or PC-board 124 through main housing 160. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 160 may also have a flat surface 164 (or other geometry) forming a galley that is configured to allow the vaporized substance and air to pass between the main housing 160 and the main shell 102. Once the vaporized substance and air pass by main housing 160, they may travel through passageway 112-1, passageway 116-1, and opening 114-1 to be inhaled by a user of personal vaporizer unit 100. The exterior of main housing 160 may also have one or more standoffs 167 (or other geometries) that are configured to allow air and the vaporized substance to reach the passageway formed by flat surface 164 and main shell 102.

Figure 25:
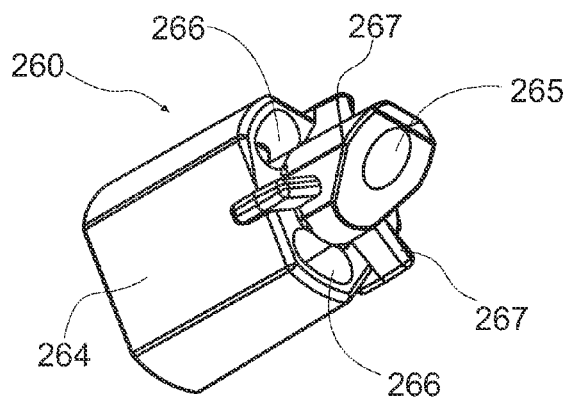
FIG. 25 is a perspective view of a main housing of a personal vaporizer unit.
Figure 26:
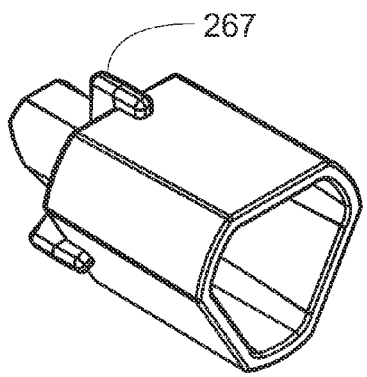
FIG. 26 is a second perspective view of the main housing of FIG. 25.
Figure 27:
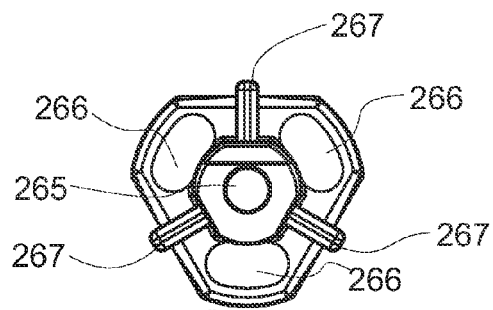
FIG. 27 is a distal end view of the main housing of FIG. 25.
Figure 29:
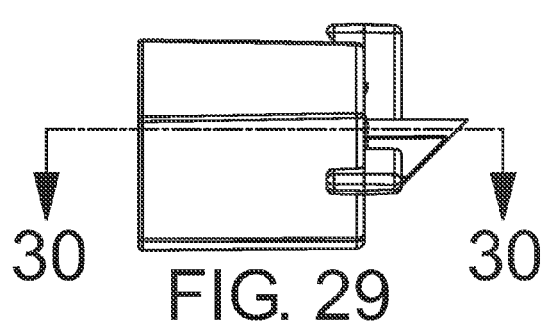
FIG. 29 is a side view of the main housing of FIG. 25.
Figure 28:
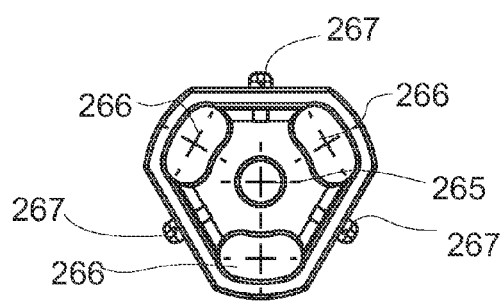
FIG. 28 is a proximal end view of the main housing of FIG. 25.
Figure 30:
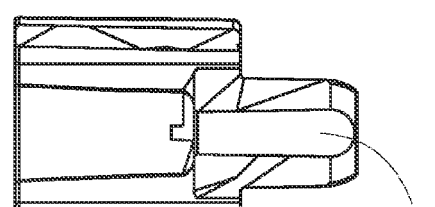
FIG. 30 is a cross-section of the main housing along the cut line shown in FIG. 29.

FIG. 25 is a perspective view of a main housing of a personal vaporizer unit. FIG. 26 is a second perspective view of the main housing of FIG. 25. FIG. 27 is a distal end view of the main housing of FIG. 25. FIG. 28 is a proximal end view of the main housing of FIG. 25. FIG. 29 is a side view of the main housing of FIG. 25. FIG. 30 is a cross-section of the main housing along the cut line shown in FIG. 29. Main housing 260 may be used as an alternative embodiment to main housing 160.

Main housing 260 is configured to hold PC-boards 123 and 124, and spacer 128. Main housing 260 is configured to fit within main shell 102 via a friction fit. Main housing 260 has several holes 266 that allow light generated by a light source(s) on PC-board 124 to pass. Once this light passes through holes 266, it may be coupled into light pipe sleeve 140 where it is conducted to a visible location on the outside of personal vaporizer unit 100.

Main housing 260 also has a hole 265 that allows an electrical conductor (not shown) to run from PC-board 123 or PC-board 124 through main housing 260. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 260 may also have flat surfaces 264 (or other geometry) that form a galley that is configured to allow the vaporized substance and air to pass between the main housing 260 and the main shell 102. Once the vaporized substance and air pass by main housing 260, they may travel through passageway 112-1, passageway 116-1, and opening 114-1 to be inhaled by a user of personal vaporizer unit 100. The exterior of main housing 260 may also have one or more standoffs 267 (or other geometries) that are configured to allow air and the vaporized substance to reach the passageway formed by flat surfaces 264 and main shell 102.

Figure 31:
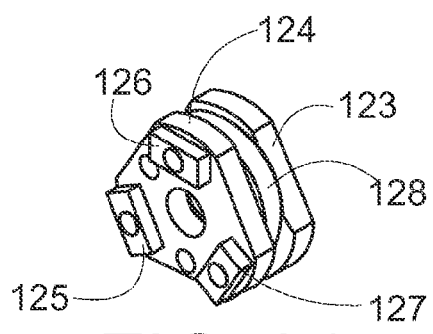
FIG. 31 is a perspective view of a printed circuit board (PCB or PC-board) assembly of a personal vaporizer unit.
Figure 32:
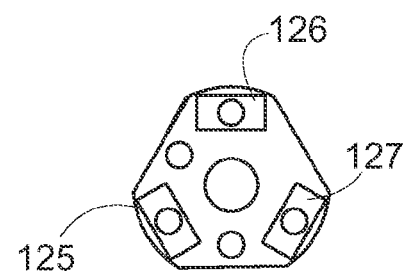
FIG. 32 is a distal end view of the PCB assembly of FIG. 31.
Figure 33:
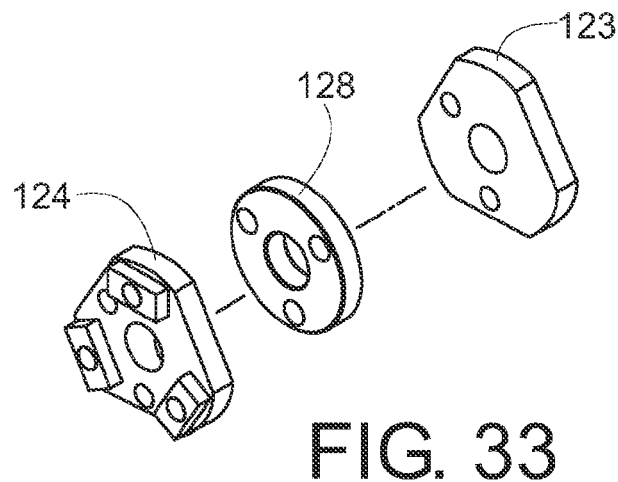
FIG. 33 is a perspective exploded view of the PCB assembly of FIG. 31.
Figure 34:
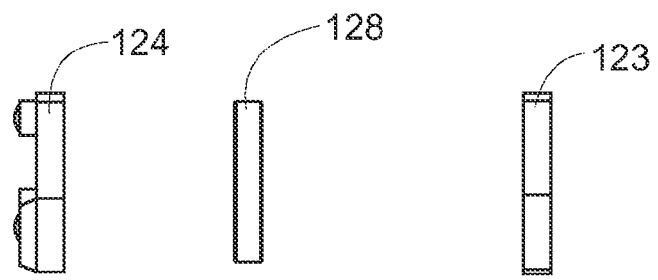
FIG. 34 is a side exploded view of the PCB assembly of FIG. 31.

FIG. 31 is a perspective view of a printed circuit board assembly of a personal vaporizer unit. FIG. 32 is a distal end view of the PCB assembly of FIG. 31. FIG. 33 is a perspective exploded view of the PCB assembly of FIG. 31. FIG. 34 is a side exploded view of the PCB assembly of FIG. 31. As can be seen in FIGS. 31-34, the PCB assembly is comprised of PC-board 123 and PC-board 124 separated by a spacer 128. PC-board 124 may have mounted upon it light emitting diodes (LEDs) 125-127 or other light sources. LEDs 125-127 are configured and positioned such that when they produce light, that light passes through holes 166 or 266 in main housings 160 and 260, respectively. This light may then be conducted by light pipe sleeve 140 to a location where it will be visible exterior to personal vaporizer unit 100.

PC-board 123 may have mounted on it a microprocessor, memory, or other circuitry (not shown) to activate or otherwise control personal vaporizer unit 100. This microprocessor may store data about the operation of personal vaporizer unit 100 in the memory. For example, the microprocessor may determine and store the number of cycles personal vaporizer unit 100 has been triggered. The microprocessor may also store a time and/or date associated with one or more of these cycles. The microprocessor may cause this data to be output via a connector. The connector may be comprised of the first and second conductive surfaces of mouthpiece 116 and/or main shell 102.

In an embodiment, the microprocessor may determine a duration associated with various cycles where personal vaporizer unit 100 has been triggered. These durations (or a number based on these duration, such as an average) may be stored in the memory. The microprocessor may cause these numbers to be output via the connector. The microprocessor may determine an empty cartridge condition and stores a number associated with a number of times said empty cartridge condition occurs. The microprocessor, or other circuitry, may determine an empty cartridge condition determined based on a resistance between atomizer housing 132 or 232 and a wick 134, 234, 136, or 236. The microprocessor may also store a time and/or date associated with one or more of these empty cartridge conditions. The number of times an empty cartridge condition is detected, and or times and/or dates associated with these empty cartridge conditions may be output via the connector.

Battery 104, PC-board 123, PC-board 124, and all electronics internal to personal vaporizer unit 100 may be sealed in a plastic or plastic and epoxy compartment within the device. This compartment may include main housing 160 or 260. All penetrations in this compartment may be sealed. Thus, only wires will protrude from the compartment. The compartment may be filled with epoxy after the assembly of battery 104, PC-board 123, PC-board 124, and LEDs 125-127. The compartment may be ultrasonically welded closed after assembly of battery 104, PC-board 123, PC-board 124, and LEDs 125-127. This sealed compartment is configured such that all vapor within personal vaporizer unit 100 does not come in contact with the electronics on PC-boards 123 or 124.

Figure 35:
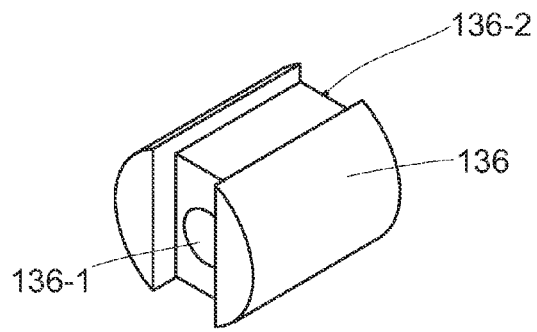
FIG. 35 is a perspective view of a proximal wick element of a personal vaporizer unit.
Figure 35A:
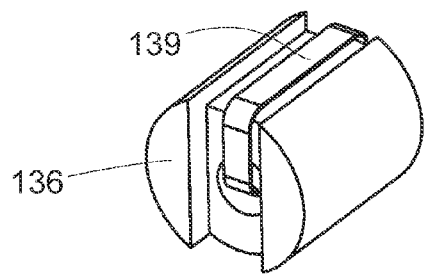
FIG. 35A is a perspective view of a heating element disposed through a proximal wick element of a personal vaporizer unit.
Figure 35B:
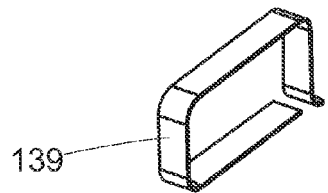
FIG. 35B is a perspective view of a heating element of a personal vaporizer unit.
Figure 36:
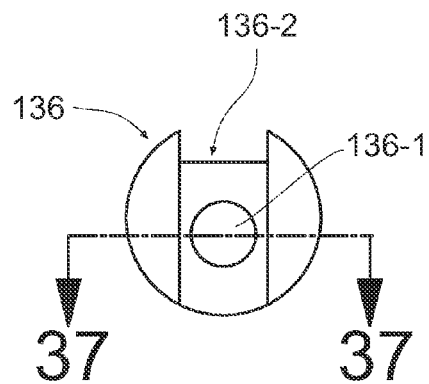
FIG. 36 is a distal end view of the wick element of FIG. 35.
Figure 37:
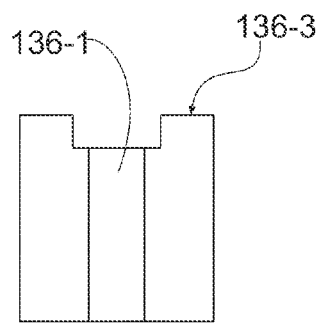
FIG. 37 is a cross-section of the wick element along the cut line shown in FIG. 35.

FIG. 35 is a perspective view of a proximal wick element of a personal vaporizer unit. FIG. 35A is a perspective view of a heating element disposed through a proximal wick element of a personal vaporizer unit. FIG. 35B is a perspective view of a heating element of a personal vaporizer unit. FIG. 36 is a distal end view of the wick element of FIG. 35. FIG. 37 is a cross-section of the wick element along the cut line shown in FIG. 35. Proximal wick 136 is configured to fit within atomizer housing 132. As can be seen in FIGS. 35-37, proximal wick 136 includes internal wire passageway 136-1 and external wire passageway 136-2. These wire passageways allows a conductor or a heating element 139 to be positioned through proximal wick 136 (via internal wire passageway 136-1). This conductor or heating element 139 may also be positioned in external wire passageway 136-2. Thus, as shown in FIG. 35A, a conductor or heating element 139 may be wrapped around a portion of proximal wick 136 by running the conductor or heating element 139 through internal wire passageway 136-1, around the distal end of proximal wick 136, and through external wire passageway 136-2 to return to approximately its point of origin. The heating element 139 may, when personal vaporizer 100 is activated, heat proximal wick 136 in order to facilitate vaporization of a substance.

Figure 38:
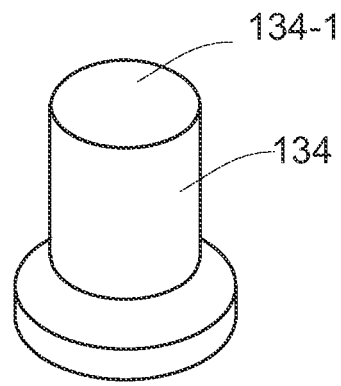
FIG. 38 is a perspective view of a distal wick element of a personal vaporizer unit.
Figure 39:
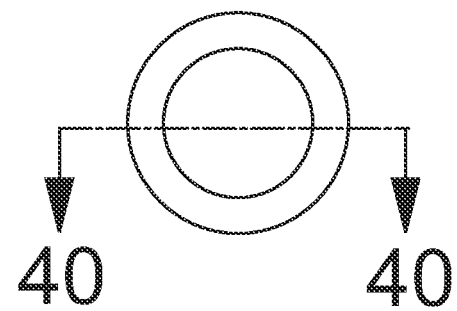
FIG. 39 is a distal end view of the wick element of FIG. 38.
Figure 40:
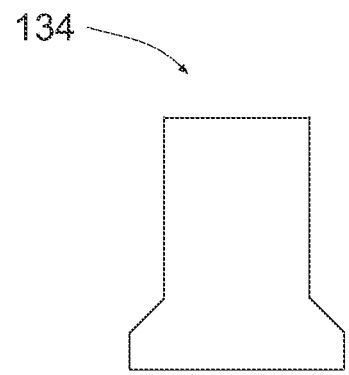
FIG. 40 is a cross-section of the wick element along the cut line shown in FIG. 39.

FIG. 38 is a perspective view of a distal wick element of a personal vaporizer unit. FIG. 39 is a distal end view of the wick element of FIG. 38. FIG. 40 is a cross-section of the wick element along the cut line shown in FIG. 39. Distal wick 134 is configured to fit within atomizer housing 132. As can be seen in FIGS. 38-40, distal wick 134 comprises two cylinders of different diameters. A chamfered surface transitions from the smaller diameter of the distal end of distal wick 134 to a larger diameter at the proximal end of distal wick 134. The cylinder at the distal end terminates with a flat surface end 134-1. This flat surface end 134-1 is the end of distal wick 134 is a surface that is placed in direct contact with a substance to be vaporized when cartridge 150 is inserted into the distal end of personal vaporizer 100. The proximal end of distal wick 134 is typically in contact with proximal wick 136. However, at least a part of proximal wick 136 and distal wick 134 are separated by an air gap. When distal wick 134 and proximal wick 136 are used together, this air gap is formed between distal wick 134 and proximal wick 136 by stand offs 136-3 as shown in FIG. 37.

Figure 41:
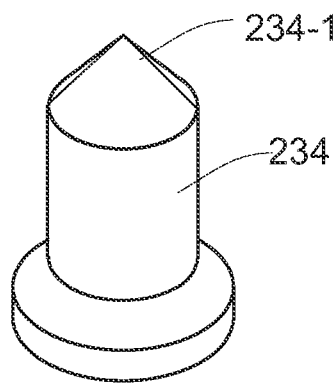
FIG. 41 is a perspective view of a distal wick element of a personal vaporizer unit.
Figure 42:
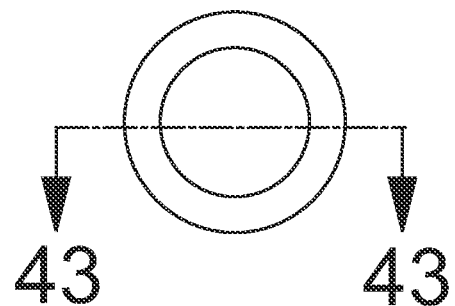
FIG. 42 is a distal end view of the wick element of FIG. 41.
Figure 43:
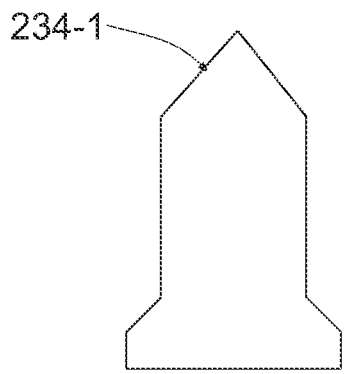
FIG. 43 is a cross-section of the wick element along the cut line shown in FIG. 42.

FIG. 41 is a perspective view of a distal wick element of a personal vaporizer unit. FIG. 42 is a distal end view of the wick element of FIG. 41. FIG. 43 is a cross-section of the wick element along the cut line shown in FIG. 42. Proximal wick 234 may be used as an alternative embodiment to distal wick 134. Proximal wick 234 is configured to fit within atomizer housing 232. As can be seen in FIGS. 41-43, proximal wick 234 comprises two cylinders of different diameters, and a cone or pointed end 234-1. A chamfered surface transitions from the smaller diameter of the distal end of proximal wick 234 to a larger diameter at the proximal end of proximal wick 234. The cylinder at the distal end terminates with a pointed end 234-1. This pointed end 234-1 is the end of proximal wick 234 that is in direct contact with a substance to be vaporized. This pointed end 234-1 may also break a seal on cartridge 150 to allow the substance to be vaporized to come in direct contact with proximal wick 234. The proximal end of proximal wick 234 is typically in contact with proximal wick 136. However, at least a part of proximal wick 136 and proximal wick 234 are separated by an air gap. When distal wick 134 and proximal wick 236 are used together, this air gap is formed between proximal wick 234 and proximal wick 136 by stand offs 136-3 as shown in FIG. 37.

Figure 44:
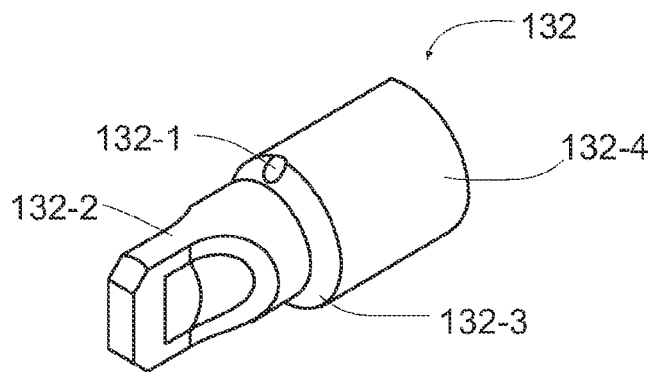
FIG. 44 is a perspective view of an atomizer housing of a personal vaporizer unit.
Figure 45:
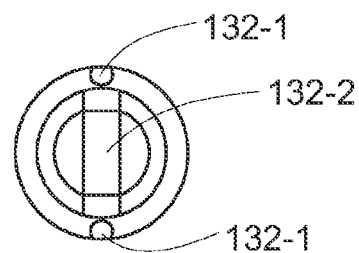
FIG. 45 is a distal end view of the atomizer housing of FIG. 44.
Figure 46:
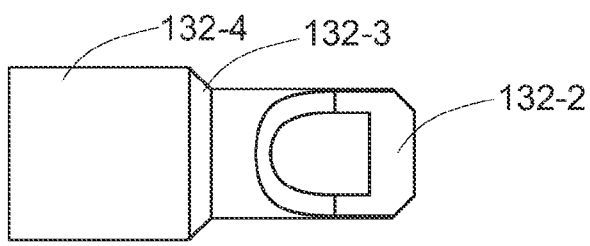
FIG. 46 is a side view of the atomizer housing of FIG. 44.
Figure 47:
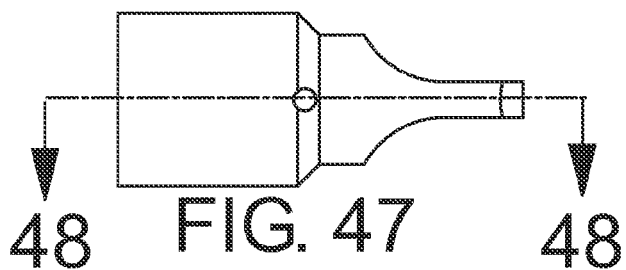
FIG. 47 is a top view of the atomizer housing of FIG. 44.
Figure 48:
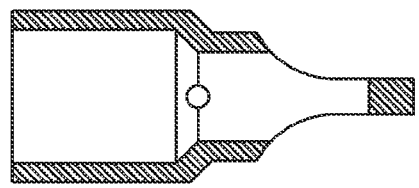
FIG. 48 is a cross-section of the atomizer housing along the cut line shown in FIG. 47.

FIG. 44 is a perspective view of an atomizer housing of a personal vaporizer unit. FIG. 45 is a distal end view of the atomizer housing of FIG. 44. FIG. 46 is a side view of the atomizer housing of FIG. 44. FIG. 47 is a top view of the atomizer housing of FIG. 44. FIG. 48 is a cross-section of the atomizer housing along the cut line shown in FIG. 47. Atomizer housing 132 is configured to fit within main shell 102. As can be seen in FIGS. 44-48, atomizer housing 132 comprises roughly two cylinders of different diameters. A chamfered surface 132-3 transitions from the smaller diameter of the distal end of atomizer housing 132 to a larger diameter at the proximal end of atomizer housing 132. The larger diameter at the proximal end of atomizer housing 132 is configured to be press fit into light pipe sleeve 140. The cylinder at the distal end terminates with a spade shaped tip 132-2. This spade shaped tip 132-2 may break a seal on cartridge 150 to allow the substance to be vaporized to come in direct contact with distal wick 134. Other shaped tips are possible (e.g., needle or spear shaped).

Chamfered surface 132-3 has one or more holes 132-1. These holes allow air to pass, via suction, through atomizer housing 132 into distal wick 134. This suction may be supplied by the user of personal vaporizer 100 sucking or inhaling on mouthpiece cover 114 and/or mouthpiece 116. The air that is sucked into distal wick 134 enters distal wick 134 on or near the chamfered surface between the two cylinders of distal wick 134. The air that is sucked into distal wick 134 displaces some of the substance being vaporized that has been absorbed by distal wick 134 causing it to be atomized as it exits distal wick 134 into the air gap formed between distal wick 134 and proximal wick 136. The heating element disposed around proximal wick 136 may then vaporize at least some of the atomized substance. In an embodiment, one or more holes 132-1 may range in diameter between 0.02 and 0.0625 inches.

In an embodiment, placing holes 132-1 at the leading edge of the chamfered surface places a set volume of the substance to be vaporized in the path of incoming air. This incoming air has nowhere to go but through the large diameter (or "head") end of the distal end wick 134. When the air enters this area in distal end wick 134 it displaces the substance to be vaporized that is suspended in distal end wick 134 towards an air cavity between distal end wick 134 and proximal end wick 136. When the displaced substance to be vaporized reaches the surface of distal end wick 134, it is forced out of the wick by the incoming air and the negative pressure of the cavity. This produces an atomized cloud of the substance to be vaporized. In an embodiment, the diameter of the head of distal end wick 134 may be varied and be smaller than the diameter of the proximal end wick 136. This allows for a tuned volume of air to bypass proximal end wick 136 and directly enter the cavity between distal wick 134 and distal wick 136 without first passing through distal wick 136.

Figure 49:
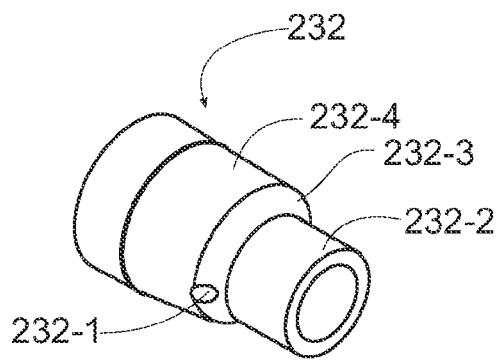
FIG. 49 is a perspective view of an atomizer housing of a personal vaporizer unit.
Figure 50:
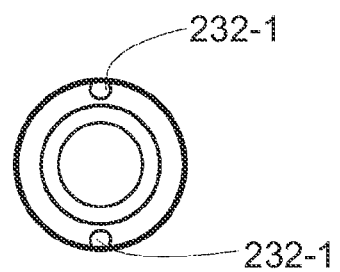
FIG. 50 is a distal end view of the atomizer housing of FIG. 49.
Figure 51:
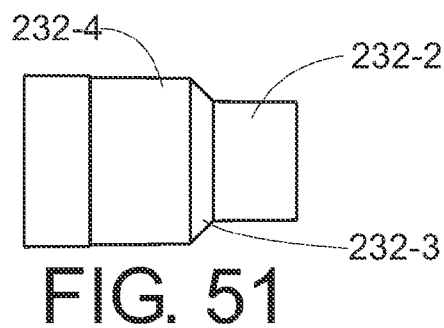
FIG. 51 is a side view of the atomizer housing of FIG. 49.
Figure 52:
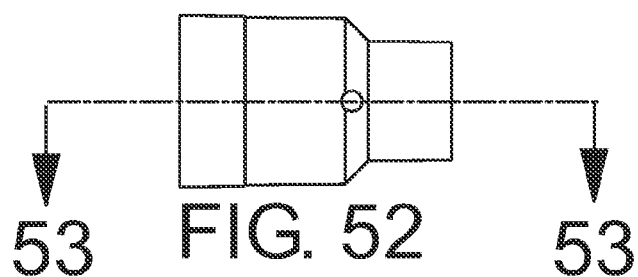
FIG. 52 is a top view of the atomizer housing of FIG. 49.
Figure 53:
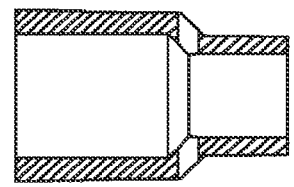
FIG. 53 is a cross-section of the atomizer housing along the cut line shown in FIG. 52.

FIG. 49 is a perspective view of an atomizer housing of a personal vaporizer unit. FIG. 50 is a distal end view of the atomizer housing of FIG. 49. FIG. 51 is a side view of the atomizer housing of FIG. 49. FIG. 52 is a top view of the atomizer housing of FIG. 49. FIG. 53 is a cross-section of the atomizer housing along the cut line shown in FIG. 52. Atomizer housing 232 is an alternative embodiment, for use with proximal wick 234, to atomizer house 132. Atomizer housing 232 is configured to fit within main shell 102 and light pipe sleeve 140. As can be seen in FIGS. 49-53, atomizer housing 232 comprises roughly two cylinders of different diameters. A chamfered surface 232-3 transitions from the smaller diameter of the distal end of atomizer housing 232 to a larger diameter at the proximal end of atomizer housing 232. The larger diameter at the proximal end of atomizer housing 232 is configured to be press fit into light pipe sleeve 140. The cylinder at the distal end terminates with an open cylinder tip 232-2. This open cylinder tip 232-2 allows the pointed end 234-1 of proximal wick 234 to break a seal on cartridge 150 to allow the substance to be vaporized to come in direct contact with proximal wick 234.

Chamfered surface 232-3 has one or more holes 232-1. These holes allow air to pass, via suction, through atomizer housing 232 into proximal wick 234. The air that is sucked into proximal wick 234 enters proximal wick 234 on or near the chamfered surface between the two cylinders of proximal wick 234. The air that is sucked into proximal wick 234 displaces some of the substance being vaporized that has been absorbed by proximal wick 234 causing it to be atomized as it exits proximal wick 234 into the air gap formed between proximal wick 234 and proximal wick 136. The heating element disposed around proximal wick 136 may then vaporize at least some of the atomized substance being vaporized. In an embodiment, one or more holes 232-1 may range in diameter between 0.02 and 0.0625 inches.

In an embodiment, placing holes 232-1 at the leading edge of the chamfered surface places a set volume of the substance to be vaporized in the path of incoming air. This incoming air has nowhere to go but through the head of the distal end wick 234. When the air enters this area in distal end wick 234 it displaces the substance to be vaporized that is suspended in distal end wick 234 towards an air cavity between distal end wick 234 and proximal end wick 236. When the displaced substance to be vaporized reaches the surface of distal end wick 232, it is forced out of the wick by the incoming air and the negative pressure of the cavity. This produces an atomized cloud of the substance to be vaporized. In an embodiment, the diameter of the head of distal end wick 234 may be varied and be smaller than the diameter of the proximal end wick 236. This allows for a tuned volume of air to bypass distal wick 236 and directly enter the cavity between proximal wick 234 and distal wick 236 without first passing through distal wick 236.

FIG. 54 is a perspective view of an atomizer housing and wicks of a personal vaporizer unit. FIG. 55 is an exploded view of the atomizer housing, wire guides, and wicks of FIG. 54. FIG. 56 is a side view of the atomizer housing and wicks of FIG. 54. FIG. 57 is a distal end view of the atomizer housing and wicks of FIG. 54. FIG. 58 is a cross-section of the atomizer housing and wicks along the cut line shown in FIG. 57. The atomizer housing and wicks shown in FIGS. 54-58 is an alternative embodiment for use with proximal wick 236. The embodiment shown in FIGS. 54-58 use atomizer housing 232, proximal wick 234, proximal wick 236, wire guide 237, and wire guide 238. Proximal wick 236 is configured to fit within atomizer housing 232. As can be seen in FIGS. 54-58, proximal wick 236 includes internal wire passageway 236-1. This wire passageway 236-1 allows a conductor or a heating element (not shown) to be positioned through proximal wick 236 (via internal wire passageway 236-1). The conductor or heating element may be positioned around wire guide 237 and wire guide 238. Thus, a conductor or heating element may run the through wire passageway 236-1, around wire guides 237 and 238, and then back through wire passageway 236-1 to return to approximately its point of origin. The heating element may, when personal vaporizer unit 100 is activated, heat proximal wick 236 in order to facilitate vaporization of a substance.

Figure 59:
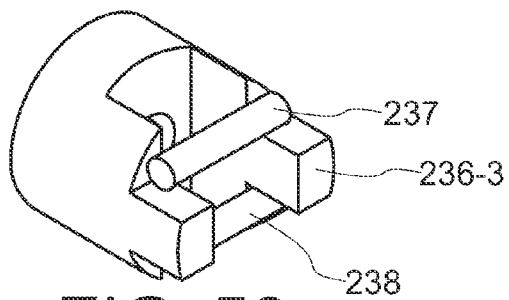
FIG. 59 is a perspective view of the proximal end wick and wire guides of FIGS. 54-58.
Figure 59A:
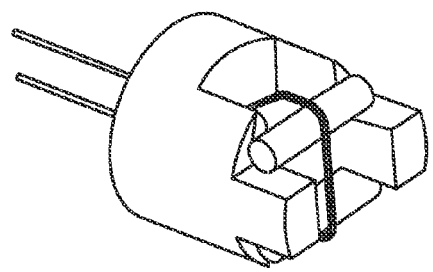
FIG. 59A is a perspective view showing a heating element disposed through the proximal end wick and around the wire guides of FIGS. 54-58.
Figure 59B:
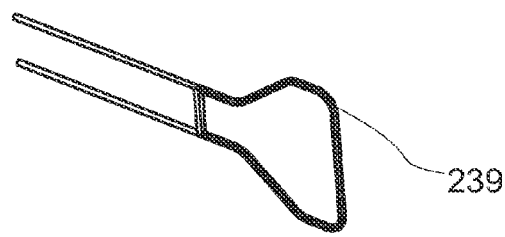
FIG. 59B is a perspective view of the heating element of a personal vaporizer unit.
Figure 60:
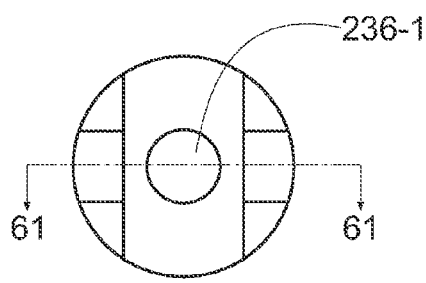
FIG. 60 is a distal end view of the wick element of FIGS. 54-58.
Figure 61:
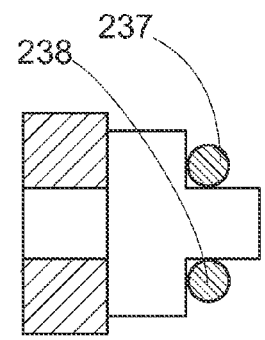
FIG. 61 is a cross-section of the wick element and wire guides along the cut line shown in FIG. 60.

FIG. 59 is a perspective view of the proximal end wick assembly of FIGS. 54-58. FIG. 59A is a perspective view showing a heating element disposed through the proximal end wick and around the wire guides of FIGS. 54-58. FIG. 59B is a perspective view of the heating element of a personal vaporizer unit. FIG. 60 is a distal end view of the wick element and wire guides of FIGS. 54-58. FIG. 61 is a cross-section of the wick element and wire guides along the cut line shown in FIG. 60. As can be seen in FIG. 59A, a conductor or heating element 239 may run through wire passageway 236-1, around wire guides 237 and 238, and then back through wire passageway 236-1 to return to approximately its point of origin.

In an embodiment, distal wicks 134, 234, and proximal wicks 136, 236, may be made of, or comprise, for example a porous ceramic. Distal wicks 134, 234, and proximal wicks 136, 236, may be made of, or comprise aluminum oxide, silicon carbide, magnesia partial stabilized zirconia, yttria tetragonal zirconia polycrystal, porous metal (e.g., steel, aluminum, platinum, titanium, and the like), ceramic coated porous metal, woven metal, spun metal, metal wool (e.g., steel wool), porous polymer, porous coated polymer, porous silica (i.e., glass), and/or porous Pyrex. Distal wicks 134, 234, and proximal wicks 136, 236, may be made of or comprise other materials that can absorb a substance to be vaporized.

The conductor or heating element that is disposed through proximal wick 136 or 236 may be made of, or comprise, for example: nickel chromium, iron chromium aluminum, stainless steel, gold, platinum, tungsten molybdenum, or a piezoelectric material. The conductor or heating element that is disposed through proximal wick 136 can be made of, or comprise, other materials that become heated when an electrical current is passed through them.

Figure 62:
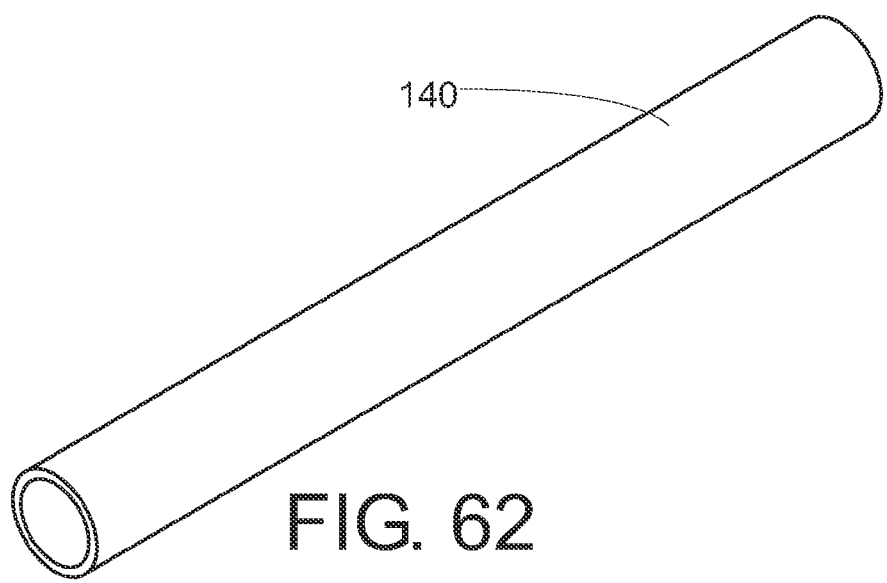
FIG. 62 is a perspective view of a light pipe sleeve of a personal vaporizer unit.
Figure 63:
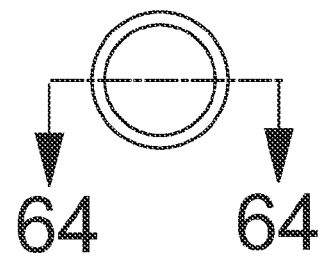
FIG. 63 is an end view of the light pipe sleeve of FIG. 62.
Figure 64:
FIG. 64 is a cross-section of the light pipe sleeve along the cut line shown in FIG. 63.

FIG. 62 is a perspective view of a light pipe sleeve of a personal vaporizer unit. FIG. 63 is an end view of the light pipe sleeve of FIG. 62. FIG. 64 is a cross-section of the light pipe sleeve along the cut line shown in FIG. 63. Light pipe sleeve 140 is configured to be disposed within main shell 102. Light pipe sleeve 140 is also configured to hold cartridge 150 and atomizer housing 132 or 232. As discussed previously, light pipe sleeve 140 is configured to conduct light entering the proximal end of light pipe sleeve 140 (e.g., from LEDs 125-127) to the distal end of light pipe sleeve 140. Typically, the light exiting the distal end of light pipe sleeve 140 will be visible from the exterior of personal vaporizer 100. The light exiting the distal end of light pipe sleeve 140 may be diffused by cartridge 150. The light exiting the distal end of light pipe sleeve 140 may illuminate characters and/or symbols drawn, printed, written, or embossed, etc., in an end of cartridge 150. In an embodiment, light exiting light pipe sleeve 140 may illuminate a logo, characters and/or symbols cut through outer main shell 102. In an embodiment, light pipe sleeve 140 is made of, or comprises, a translucent acrylic plastic.

FIG. 65 is a perspective view of a cartridge of a personal vaporizer unit. FIG. 66 is a proximal end view of the cartridge of FIG. 65. FIG. 67 is a side view of the cartridge of FIG. 65. FIG. 68 is a top view of the cartridge of FIG. 65. FIG. 69 is a cross-section of the cartridge along the cut line shown in FIG. 66. As shown in FIGS. 65-69, cartridge 150 comprises a hollow cylinder section with at least one exterior flat surface 158. The flat surface 158 forms, when cartridge 150 is inserted into the distal end of personal vaporizer unit 100, an open space between the exterior surface of the cartridge and an interior surface of light pipe sleeve 140. This space defines a passage for air to be drawn from outside personal vaporizer unit 100, through personal vaporizer unit 100 to be inhaled by the user along with the vaporized substance. This space also helps define the volume of air drawn into personal vaporizer unit 100. By defining the volume of air typically drawn into the unit, different mixtures of vaporized substance to air may be produced.

The hollow portion of cartridge 150 is configured as a reservoir to hold the substance to be vaporized by personal vaporizer unit 100. The hollow portion of cartridge 150 holds the substance to be vaporized in direct contact with distal wick 134 or 234. This allows distal wick 134 or 234 to become saturated with the substance to be vaporized. The area of distal wick 134 or 234 that is in direct contact with the substance to be vaporized may be varied in order to deliver different doses of the substance to be vaporized. For example, cartridges 150 with differing diameter hollow portions may be used to deliver different doses of the substance to be vaporized to the user.

Cartridge 150 may be configured to confine the substance to be vaporized by a cap or seal (not shown) on the proximal end. This cap or seal may be punctured by the end of atomizer housing 132, or the pointed end 234-1 of proximal wick 234.

When inserted into personal vaporizer unit 100, cartridge standoffs 157 define an air passage between the end of light pipe sleeve 140 and main shell 102. This air passage allows air to reach the air passage defined by flat surface 158.

The hollow portion of cartridge 150 also includes one or more channels 154. The end of these channels are exposed to air received via the air passage(s) defined by flat surface 158. These channels allow air to enter the hollow portion of cartridge 150 as the substance contained in cartridge 150 is drawn into a distal wick 134 or 234. Allowing air to enter the hollow portion of cartridge 150 as the substance contained in cartridge 150 is removed prevents a vacuum from forming inside cartridge 150. This vacuum could prevent the substance contained in cartridge 150 from being absorbed into distal wick 134 or 234.

In an embodiment, cartridge 150 may be at least partly translucent. Thus cartridge 150 may act as a light diffuser so that light emitted by one or more of LEDs 125-127 is visible external to personal vaporizer unit 100.

Figure 70:
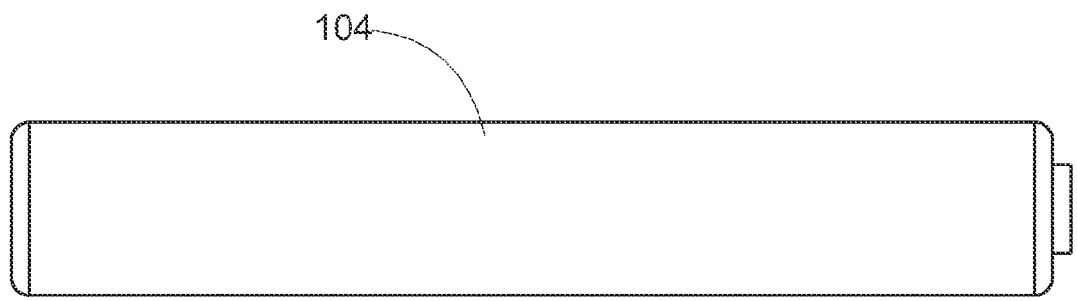
FIG. 70 is a side view of a battery of a personal vaporizer unit.
Figure 71:
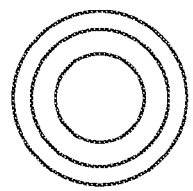
FIG. 71 is an end view of the battery of FIG. 70.
Figure 72:
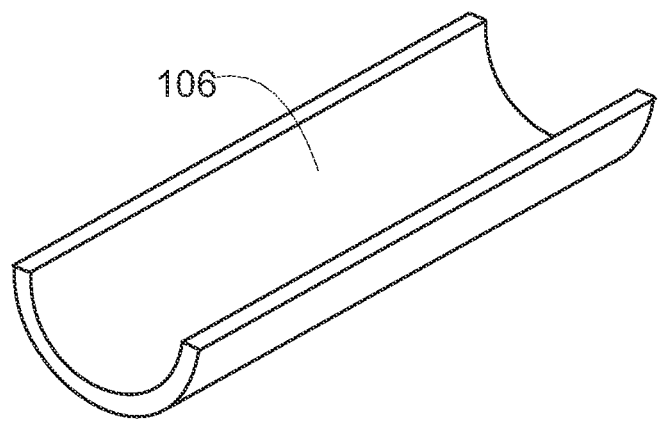
FIG. 72 is a perspective view of a battery support of a personal vaporizer unit.

FIG. 70 is a side view of a battery of a personal vaporizer unit. FIG. 71 is an end view of the battery of FIG. 70. FIG. 72 is a perspective view of a battery support of a personal vaporizer unit. As can be seen in FIG. 72, battery support 106 does not form a complete cylinder that completely surrounds battery 104. This missing portion of a cylinder forms a passageway that allows air and the vaporized substance to pass by the battery from the atomizer assembly to the mouthpiece 116 so that it may be inhaled by the user.

Figure 73:
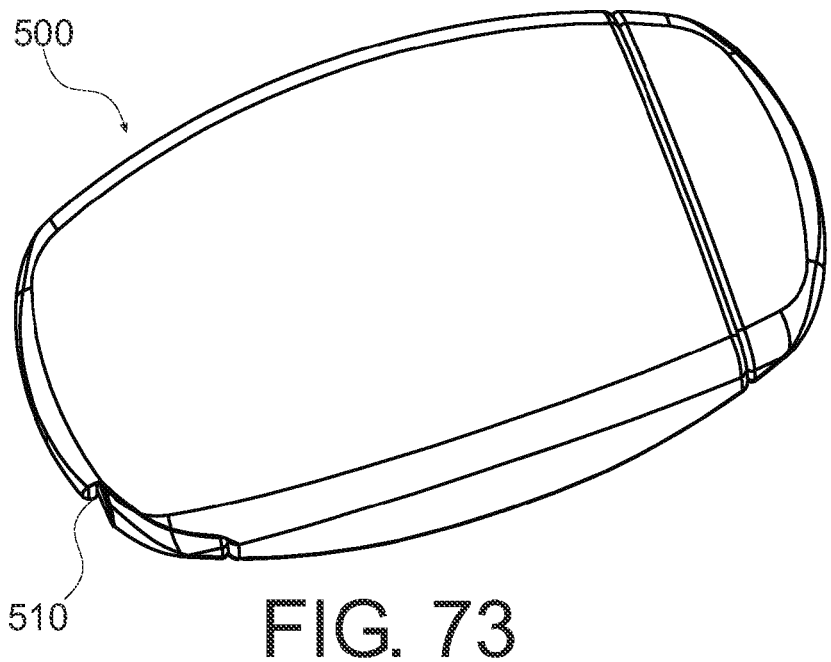
FIG. 73 is a perspective view of a personal vaporizer unit case.
Figure 74:
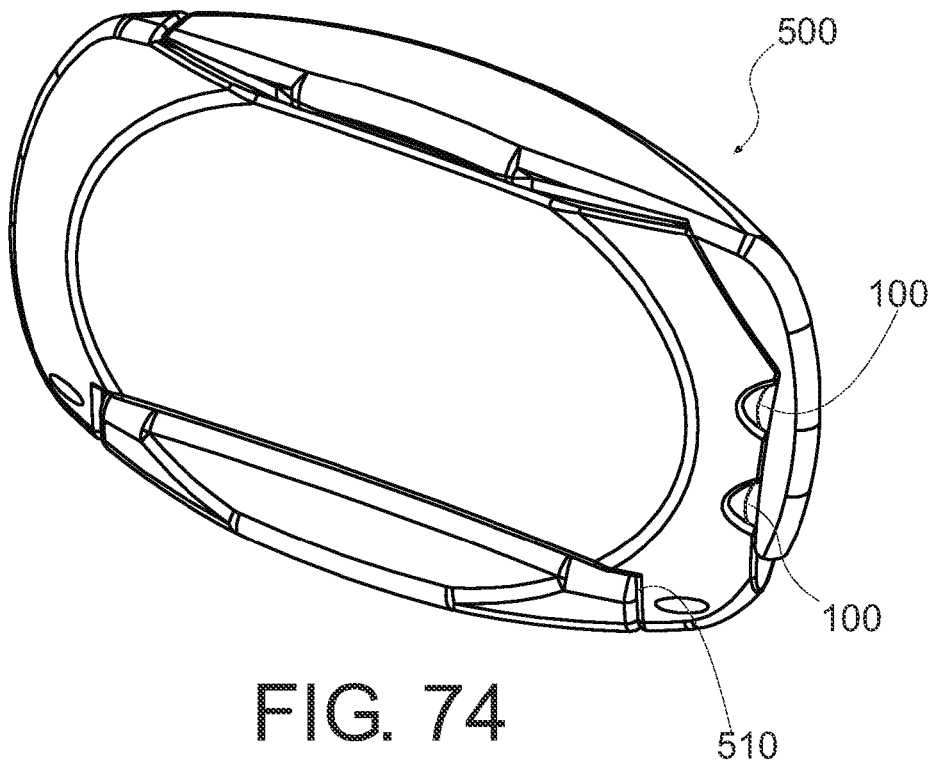
FIG. 74 is a perspective view of a personal vaporizer unit case.

FIG. 73 is a top perspective view of a personal vaporizer unit case. FIG. 74 is a bottom perspective view of a personal vaporizer unit case. Personal vaporizer case 500 is configured to hold one or more personal vaporizer units 100. Personal vaporizer case 500 includes a connector 510 to interface to a computer. This connector allows case 500 to transfer data from personal vaporizer unit 100 to a computer via connector 510. Case 500 may also transfer data from personal vaporizer unit 100 via a wireless interface. This wireless interface may comprise an infrared (IR) transmitter, a Bluetooth interface, an 802.11 specified interface, and/or communicate with a cellular telephone network. Data from a personal vaporizer unit 100 may be associated with an identification number stored by personal vaporizer unit 100. Data from personal vaporizer unit 100 may be transmitted via the wireless interface in association with the identification number.

Personal vaporizer case 500 includes a battery that may hold charge that is used to recharge a personal vaporizer unit 100. Recharging of personal vaporizer unit 100 may be managed by a charge controller that is part of case 500.

When case 500 is holding a personal vaporizer unit 100, at least a portion of the personal vaporizer unit 100 is visible from the outside of case 500 to allow a light emitted by personal vaporizer unit 100 to provide a visual indication of a state of personal vaporizer unit 500. This visual indication is visible outside of case 500.

Personal vaporizer unit 100 is activated by a change in impedance between two conductive surfaces. In an embodiment, these two conductive surfaces are part of main shell 102 and mouthpiece 116. These two conductive surfaces may also be used by case 500 to charge battery 104. These two conductive surfaces may also be used by case 500 to read data out of personal vaporizer unit 100.

In an embodiment, when a user puts personal vaporizer unit 100 in his/her mouth and provides "suction," air is drawn into personal vaporizer unit 100 though a gap between the end of main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 132, cartridge 150, and light pipe sleeve 140. Air travels to distal wick 134 via one or more holes 132-1, in chamfered surface(s) 132-3. Air travels to distal wick 234 via one or more holes 232-1, in chamfered surface(s) 232-3. Air is also allowed to enter cartridge 150 via one or more channels 154. This air entering cartridge 150 via channels 154 "back fills" for the substance being vaporized which enters distal wick 134. The substance being vaporized is held in direct contact with distal wick 134 or 234 by cartridge 150. The substance being vaporized is absorbed by and may saturate distal wick 134 or 234 and proximal wick 136 or 236.

The incoming air drawn through holes 132-1 displaces from saturated distal wick 134 the substance being vaporized. The displaced substance being vaporized is pulled from wick elements 134 into a cavity between distal wick 134 and 136. This cavity may also contain a heating element that has been heated to between 150-200° C. The displaced substance being vaporized is pulled from wick elements 134 in small (e.g., atomized) droplets. These atomized droplets are vaporized by the heating element.

In an embodiment, when a user puts personal vaporizer unit 100 in his/her mouth and provides "suction," air is drawn into personal vaporizer unit 100 though a gap between the end of main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 232, cartridge 150, and light pipe sleeve 140. Air travels to proximal wick 234 via one or more holes 232-1, in chamfered surface(s) 232-1. Air is also allowed to enter cartridge 150 via one or more channels 154. This air entering cartridge 150 via channels 154 "back fills" for the substance being vaporized which enters proximal wick 234. The substance being vaporized is held in direct contact with proximal wick 234 by cartridge 150. The substance being vaporized is absorbed by and may saturate distal wick 243 and proximal wick 236.

The incoming air drawn through holes 232-1 displaces from saturated proximal wick 234 the substance being vaporized. The displaced substance being vaporized is pulled from wick elements 234 into a cavity between wick distal wick 234 and proximal wick 236. This cavity may also contain a heating element that has been heated to between 150-200° C. The displaced substance being vaporized is pulled from distal wick 234 in small (e.g., atomized) droplets. These atomized droplets are vaporized by the heating element.

In both of the previous two embodiments, the vaporized substance and air are drawn down a galley adjacent to battery 104, through mouthpiece insulator 112, mouthpiece 116, and mouthpiece cover 114. After exiting personal vaporizer unit 100, the vapors may be inhaled by a user.

Figure 75:
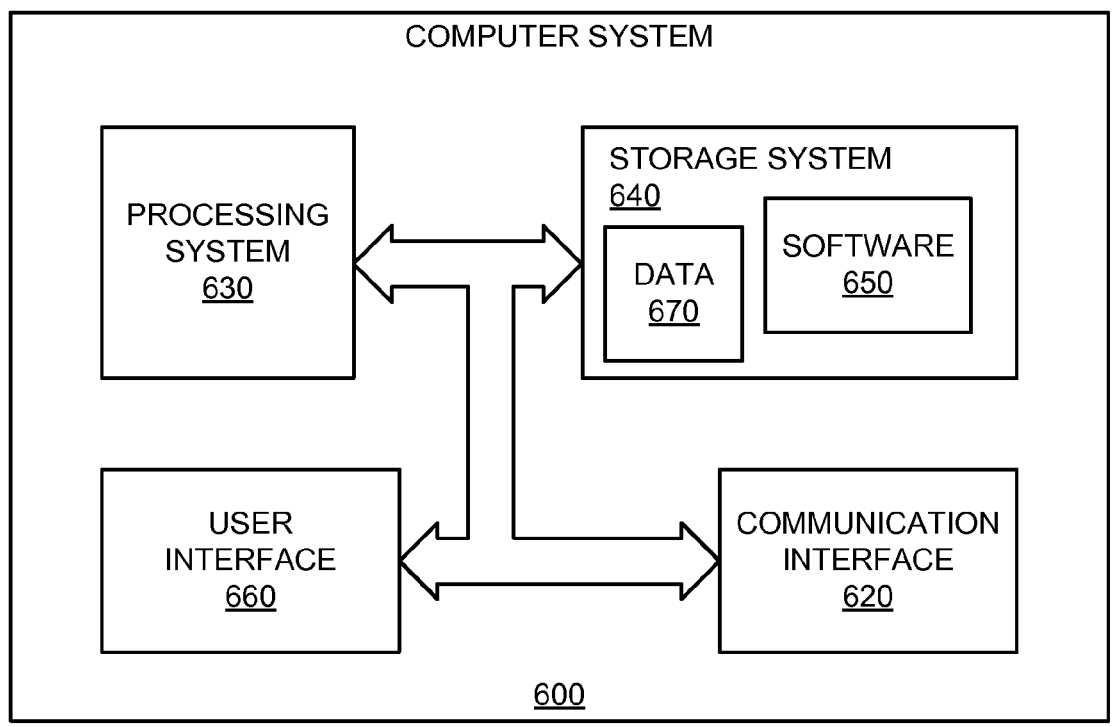
FIG. 75 is a block diagram of a computer system.

The systems, controller, and functions described above may be implemented with or executed by one or more computer systems. The methods described above may be stored on a computer readable medium. Personal vaporizer unit 100 and case 500 may be, comprise, or include computers systems. FIG. 75 illustrates a block diagram of a computer system. Computer system 600 includes communication interface 620, processing system 630, storage system 640, and user interface 660. Processing system 630 is operatively coupled to storage system 640. Storage system 640 stores software 650 and data 670. Processing system 630 is operatively coupled to communication interface 620 and user interface 660. Computer system 600 may comprise a programmed general-purpose computer. Computer system 600 may include a microprocessor. Computer system 600 may comprise programmable or special purpose circuitry. Computer system 600 may be distributed among multiple devices, processors, storage, and/or interfaces that together comprise elements 620-670.

Communication interface 620 may comprise a network interface, modem, port, bus, link, transceiver, or other communication device. Communication interface 620 may be distributed among multiple communication devices. Processing system 630 may comprise a microprocessor, microcontroller, logic circuit, or other processing device. Processing system 630 may be distributed among multiple processing devices. User interface 660 may comprise a keyboard, mouse, voice recognition interface, microphone and speakers, graphical display, touch screen, or other type of user interface device. User interface 660 may be distributed among multiple interface devices. Storage system 640 may comprise a disk, tape, integrated circuit, RAM, ROM, network storage, server, or other memory function. Storage system 640 may be a computer readable medium. Storage system 640 may be distributed among multiple memory devices.

Processing system 630 retrieves and executes software 650 from storage system 640. Processing system may retrieve and store data 670. Processing system may also retrieve and store data via communication interface 620. Processing system 650 may create or modify software 650 or data 670 to achieve a tangible result. Processing system may control communication interface 620 or user interface 670 to achieve a tangible result. Processing system may retrieve and execute remotely stored software via communication interface 620.

Software 650 and remotely stored software may comprise an operating system, utilities, drivers, networking software, and other software typically executed by a computer system. Software 650 may comprise an application program, applet, firmware, or other form of machine-readable processing instructions typically executed by a computer system. When executed by processing system 630, software 650 or remotely stored software may direct computer system 600 to operate as described herein.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A personal vaporizer unit, comprising:
   circuitry;
   a vaporizer that vaporizes a substance in response to being activated;
   a first conductive surface on a main shell configured to contact a first body part of a person holding said main shell of said personal vaporizer unit; and,
   a mouthpiece having a second conductive surface, conductively isolated from said first conductive surface, configured to contact a second body part of said person, wherein said circuitry activates said vaporizer in response to detecting a change in conductivity between said first conductive surface and said second conductive surface.

2. The personal vaporizer unit of claim 1, wherein at least one of said first conductive surface and said second conductive surface is used to pass a charging current to a battery.

3. The personal vaporizer unit of claim 1, wherein said change in conductivity comprises a drop in impedance between said first conductive surface and said second conductive surface.

4. The personal vaporizer unit of claim 1, wherein said change in conductivity comprises a change in capacitance between said first conductive surface and said second conductive surface.

5. The personal vaporizer unit of claim 1, wherein said first body part is a finger.

6. The personal vaporizer unit of claim 5, wherein said second body part is a lip.

7. The personal vaporizer unit of claim 5, wherein said second body part is a second finger.

8. A method of operating a personal vaporizing unit including circuitry, comprising:
   detecting a first impedance with said circuitry between a first conductive surface and a second conductive surface, said first conductive surface disposed on a main shell that is used to hold said personal vaporizing unit, said second conductive surface disposed on a mouthpiece of said personal vaporizing unit;
   detecting a second impedance with said circuitry between said first conductive surface and said second conductive surface;
   based on said second impedance meeting a criteria, activating said personal vaporizing unit.

9. The method of claim 8, wherein said first impedance indicates conductive isolation and said second impedance indicates electrical continuity.

10. The method of claim 8, wherein said first impedance is associated with only one of a first body part and a second body part being in contact with only one of said first conductive surface and said second conductive surface.

11. The method of claim 10, wherein said first body part is a finger.

12. The method of claim 11, wherein said second body part is a lip.

13. The method of claim 11, wherein said second body part is a second finger.

14. The method of claim 8, wherein said second impedance is associated with a first body part being in contact with said first conductive surface and a second body part being in contact with said second conductive surface.

15. The method of claim 14, wherein said first body part is a finger.

16. The method of claim 15, wherein said second body part is a lip.

17. The method of claim 15, wherein said second body part is a second finger.

18. The method of claim 8, further comprising:
   charging a battery of said personal vaporizing unit by passing a current through at least one of said first conductive surface and said second conductive surface.

19. A personal vaporizer unit, comprising:
   circuitry;
   a vaporizer that vaporizes a substance in response to being activated; a first conductive surface on a main shell configured to contact a first body part of a person holding said main shell of said personal vaporizer unit; and,
   a second conductive surface on said main shell, conductively isolated from said first conductive surface, configured to contact a second body part of said person, wherein said circuitry activates said vaporizer in response to detecting a change in conductivity between said first conductive surface and said second conductive surface.

20. The personal vaporizer unit of claim 19, wherein said first body part is a first finger and said second body part is a second finger.

* * * * *